US010384207B2

(12) United States Patent
Goodwin, Jr.

(10) Patent No.: US 10,384,207 B2
(45) Date of Patent: Aug. 20, 2019

(54) ASSAY APPARATUS AND METHODS

(71) Applicant: Neuro Probe Incorporated, Gaithersburg, MD (US)

(72) Inventor: Richard H. Goodwin, Jr., Bethesda, MD (US)

(73) Assignee: Neuro Probe Incorporated, Gaithersburg, MD (US)

( * ) Notice: Subject to any disclaimer, the term of this patent is extended or adjusted under 35 U.S.C. 154(b) by 135 days.

(21) Appl. No.: 15/213,632

(22) Filed: Jul. 19, 2016

(65) Prior Publication Data
US 2017/0021350 A1 Jan. 26, 2017

Related U.S. Application Data

(60) Provisional application No. 62/194,888, filed on Jul. 21, 2015.

(51) Int. Cl.
*B01L 3/00* (2006.01)
*G01N 33/50* (2006.01)

(52) U.S. Cl.
CPC ....... *B01L 3/5085* (2013.01); *B01L 3/502723* (2013.01); *B01L 3/502746* (2013.01); *B01L 2200/0694* (2013.01); *B01L 2300/0816* (2013.01); *B01L 2300/0867* (2013.01); *B01L 2300/161* (2013.01); *B01L 2400/0406* (2013.01); *B01L 2400/0472* (2013.01); *G01N 33/5008* (2013.01)

(58) Field of Classification Search
CPC ............... B01L 3/5085; B01L 3/502723
USPC .......................................... 506/10
See application file for complete search history.

(56) References Cited

U.S. PATENT DOCUMENTS

| | | | |
|---|---|---|---|
| 2,761,558 A | 9/1956 | McLean, Jr. et al. |
| 4,912,057 A | 3/1990 | Guirguis et al. |
| 5,200,152 A | 4/1993 | Brown |
| 5,210,021 A | 5/1993 | Goodwin, Jr. |
| 5,284,753 A | 2/1994 | Goodwin, Jr. |
| 5,302,515 A | 4/1994 | Goodwin, Jr. |
| 5,436,157 A | 7/1995 | Herr et al. |
| 5,514,555 A | 5/1996 | Springer et al. |
| 5,601,997 A | 2/1997 | Tchao |
| 5,602,005 A | 2/1997 | Herr et al. |
| 5,605,803 A | 2/1997 | Herr et al. |
| 5,716,849 A | 2/1998 | Ligon et al. |
| 5,888,807 A | 3/1999 | Palsson et al. |
| 5,906,940 A | 5/1999 | Wandrey et al. |
| 6,287,340 B1 | 11/2001 | Altman et al. |
| 6,329,164 B1 | 12/2001 | Goodwin, Jr. |
| 6,395,505 B2 | 5/2002 | Goodwin, Jr. |
| 6,468,786 B2 | 10/2002 | Goodwin, Jr. |
| 6,576,433 B1 | 6/2003 | Keller et al. |
| 6,720,143 B2 | 4/2004 | Juncosa et al. |
| 6,767,401 B2 | 7/2004 | Goodwin, Jr. |
| 6,811,752 B2 | 11/2004 | Barbera-Guillem |
| 6,833,269 B2 | 12/2004 | Carpenter |
| 6,929,945 B2 | 8/2005 | Aravanis et al. |
| 7,014,706 B2 | 3/2006 | Goodwin, Jr. |
| 7,108,966 B2 | 9/2006 | Aravanis et al. |
| 7,332,029 B2 | 2/2008 | Goodwin, Jr. |
| 7,547,525 B2 | 6/2009 | Goodwin, Jr. |
| 7,704,325 B2 | 4/2010 | Goodwin, Jr. |
| 7,795,024 B2 | 9/2010 | Madlambayan et al. |
| 8,129,175 B2 | 3/2012 | Goodwin, Jr. |
| 8,486,655 B2 | 7/2013 | Goodwin, Jr. |
| 8,679,737 B2 | 3/2014 | Zantl |
| 2002/0086280 A1 | 7/2002 | Lynes et al. |
| 2002/0146680 A1 | 10/2002 | Rich |
| 2002/0150503 A1 | 10/2002 | Tanaka et al. |
| 2003/0022363 A1 | 1/2003 | Rao |
| 2003/0044879 A1 | 3/2003 | Beyer et al. |
| 2003/0143612 A1 | 7/2003 | Ault-Riche et al. |
| 2004/0014205 A1 | 1/2004 | Banes |

(Continued)

FOREIGN PATENT DOCUMENTS

AU 2005272814 4/2011
EP 1786921 1/2011
(Continued)

OTHER PUBLICATIONS

European Office Action dated Feb. 15, 2008 in European Application No. 05785092.7.
Response to European Office Action filed Jul. 31, 2008 in European Application No. 05785092.7.
European Office Action dated Sep. 2, 2008 in European Application No. 05785092.7.
Response to European Office Action filed Mar. 12, 2009 in European Application No. 05785092.7.
European Office Action dated Mar. 27, 2009 in European Application No. 05785092.7.
Response to European Office Action filed Sep. 11, 2009 in European Application No. 05785092.7.

(Continued)

*Primary Examiner* — Karla A Dines
(74) *Attorney, Agent, or Firm* — Plumsea Law Group, LLC

(57) ABSTRACT

Apparatus and methods for determining whether a test compound induces cell activity, changes cell activity, prevents cell activity, or inhibits cell activity. An embodiment comprises placing a test compound solution in contact with a cell suspension media containing cells, diffusing the test compound solution into the cell suspension from one or more sides, and detecting activity in the cells with respect to their distance from the side from which the test compound is diffusing. Embodiments may provide an apparatus that allows a side source, a point source, or both, from which a test compound solution diffuses into a cell suspension media and contacts cells. Detecting cell activity may involve detecting activity in a first cell group proximate to the side from which the test compound is diffusing, and detecting activity in a second cell group farther than the first cell group from the side from which the test compound is diffusing.

21 Claims, 26 Drawing Sheets

(56) References Cited

U.S. PATENT DOCUMENTS

| | | |
|---|---|---|
| 2004/0071599 A1 | 4/2004 | Rusch et al. |
| 2004/0126876 A1 | 7/2004 | Ravin et al. |
| 2005/0058631 A1 | 3/2005 | Kihm et al. |
| 2005/0135974 A1 | 6/2005 | Harvey et al. |
| 2006/0182724 A1 | 8/2006 | Riordan |
| 2009/0011495 A1 | 1/2009 | Steinmann et al. |
| 2009/0232777 A1 | 9/2009 | Lundgren-Akerlund et al. |
| 2009/0311735 A1 | 12/2009 | Crook et al. |
| 2010/0009442 A1 | 1/2010 | Sasai et al. |
| 2010/0081200 A1 | 4/2010 | Rajala et al. |
| 2010/0105132 A1 | 4/2010 | Totey et al. |
| 2010/0112684 A1 | 5/2010 | Lee et al. |
| 2010/0120142 A1 | 5/2010 | Impola et al. |
| 2010/0167398 A1 | 7/2010 | Sasai et al. |
| 2010/0173410 A1 | 7/2010 | Thomson et al. |
| 2010/0173414 A1 | 7/2010 | Turovets et al. |
| 2010/0189700 A1 | 7/2010 | Lazzari et al. |
| 2010/0197013 A1 | 8/2010 | Kamp et al. |
| 2010/0227399 A1 | 9/2010 | Funaki et al. |
| 2010/0227403 A1 | 9/2010 | Xu et al. |
| 2010/0284978 A1 | 11/2010 | Weiss et al. |
| 2010/0297089 A1 | 11/2010 | Oh |
| 2010/0317101 A1 | 12/2010 | Mandalam et al. |
| 2011/0027887 A1 | 2/2011 | Gerecht-Nir et al. |
| 2011/0052549 A1 | 3/2011 | Chin et al. |
| 2011/0076320 A1 | 3/2011 | Coroneo |
| 2011/0076770 A1 | 3/2011 | Sakai et al. |
| 2011/0091930 A1 | 4/2011 | Vacanti et al. |
| 2011/0136226 A1 | 6/2011 | Navran, Jr. |
| 2011/0177597 A1 | 7/2011 | Menu et al. |
| 2011/0207175 A1 | 8/2011 | El-Sabban et al. |
| 2011/0256622 A1 | 10/2011 | West et al. |
| 2011/0256626 A1 | 10/2011 | Park et al. |
| 2011/0300112 A1 | 12/2011 | Marban et al. |
| 2012/0021509 A1 | 1/2012 | Kang et al. |
| 2012/0052577 A1 | 3/2012 | Espinosa De Los Monteros et al. |
| 2012/0064627 A1 | 3/2012 | Khine et al. |
| 2012/0070878 A1 | 3/2012 | Fink et al. |
| 2012/0122215 A1 | 5/2012 | Edinger et al. |
| 2012/0134965 A1 | 5/2012 | Kim et al. |
| 2013/0244270 A1 | 9/2013 | Xie et al. |
| 2017/0199368 A1* | 7/2017 | Goodwin ............... G02B 21/34 |

FOREIGN PATENT DOCUMENTS

| | | |
|---|---|---|
| HK | 1109427 | 4/2011 |
| JP | 08505530 | 6/1996 |
| KR | 10-0850643 B1 | 8/2008 |
| RU | 2383615 C1 | 3/2010 |
| WO | 9416098 | 7/1994 |
| WO | 0007007 | 2/2000 |
| WO | 0055298 | 9/2000 |
| WO | 2006020766 | 2/2006 |

OTHER PUBLICATIONS

European Office Action dated Sep. 23, 2009 in European Application No. 05785092.7.
Response to European Office Action filed Jan. 29, 2010 in European Application No. 05785092.7.
European Office Action dated Apr. 16, 2010 in European Application No. 05785092.7.
Response to European Office Action filed Jun. 4, 2010 in European Application No. 05785092.7.
Notice of Allowance dated Jul. 26, 2010 in European Application No. 05785092.7.
Japanese Office Action dated May 10, 2011 in Japanese Application No. 2007525788, with English translation.
Response to Japanese Office Action filed Aug. 26, 2011 in Japanese Application No. 2007525788, with English translation.
Canadian Office Action dated Jan. 18, 2012 in Canadian Application No. 2,576,431.
Response to Canadian Office Action filed Jul. 16, 2012 in Canadian Application No. 2,576,431.
Japanese Office Action dated Mar. 21, 2012 in Japanese Application No. 2007525788, with English translation.
Response to Japanese Office Action filed Jul. 2, 2012 in Japanese Application No. 2007525788, with English translation.
Manabu Yoshida, Makiko Ishikawa, Hiroko Izumi, Rosaria De Santis and Masaaki Morisawa"Store-operated calcium channel regulates chemotactic behavior of ascidian sperm"; Misaki Marine Biological Station, Graduate School of Science, University of Tokyo, Miura, Kanagawa 238-0225, Japan; and Laboratory of Cell Biology, Stazione Zoologica Anton Dohrn, Villa Comunale, 80121 Naples, Italy; www.pnas.org/cgi/doi/10.1073/pnas.0135565100; PNAS, Jan. 7, 2003, vol. 100, No. 1, 149-154.
Andrew J. Muinonen-Martin, Douwe M. Veltman, Gabriela Kalna & Robert H. Insall, "An Improved Chamber for Direct Visualisation of Chemotaxis", [online] , Dec. 2010, vol. 5, Issue 12, Published by Public Library of Science, PLos ONE, pone.0015309, retrieved from the internet<URL:http://journals.plos.org/plosone/article?id=10.1371/journal.pone.0015309.
Eric K. Sackmann, Anna L. Fulton & David J. Beebe, "The present and future role of microfluidics in biomedical research", [online] Nature Review, Mar. 2014, vol. 507, pp. 181-189, Published by McMillan Publishers Limited, retrieved from the internet:<URL:http://www.nature.com/nature/journal/v507/n7491/full/nature13118.html.
Journal of Immunological Methods "Rapid flourescence-based measurement of neutrophil migration in vitro"; C.W.Frevert, V.A. Wong, R.B. Goodman, R. Goodwin and T.R. Martin; Aug. 1997.
Journal of Immunological Methods "Improved rapid photometric assay for quantitative measurement of PMN migration"; W.G. Junger, T.A. Cardoza, F.C. Liu, D.B. Hoyt and R. Goodwin; Aug. 1992.
"Spatial Control of Actin Polymerization During Neutrophil Chemotaxis" by Orin D. Weiner, Guy Servant, Matthew D. Welch, Timothy J. Mitchison, John W. Sedat and Henry R. Bourne; Nature Cell Biology—vol. 1—Jun. 1999; http://www.cellbio.nature.com.
Robert D. Nelson, et al., "Chemotaxis under Agarose: A New and Simple method for Measuring Chemotaxis and Spontaneous Migration of human Polymorphonuclear Leukocytes and Monocytes", J. Immunology 1975, pp. 1650-1656, vol. 115(6), The Williams & Wilkins Co.
"Dictyostelium Chemotactic Response to Spatial and Temporal Gradients. Theories of the Limits of Chemotactic Sensitivity and of Pseudochemotaxis" by R.P. Futrelle; Biology and Computing Research Group, Department of Genetics and Development; University of Illinois, Urbana, Illinois 61801; Journal of Cellular Biochemistry 18:197-212 (1982), Cellular Recognition 603-618.
Decision to Grant a European Patent dated Dec. 16, 2010 in European Application No. 05785092.7.
Australian Office Action dated Sep. 6, 2010 in Australian Application No. 2005272814.
Response to Australian Office Action filed Dec. 2, 2010 in Australian Application No. 2005272814.
Notice of Acceptance dated Dec. 14, 2010 in Australian Application No. 2005272814.
Notification of Transmittal of the International Search Report and the Written Opinion of the International Searching Authority, or the Declaration dated Mar. 7, 2006 in PCT/US05/28546.
Supplementary European Search Report dated Nov. 7, 2007 in European Application No. 05785092.
International Search Report and Written Opinion dated Oct. 13, 2016 in International Application No. PCT/US2016/043087.
Xie, Lan et al., "Integration of Sperm Motility and Chemotaxis Screening with a Microchannel-Based Device," Clinical chemistry, 2010, vol. 56 (8), pp. 1270-1278.
Extended European Search Report dated Dec. 14, 2018 in European Patent Application No. 16828447.9.
Office Action dated Jan. 8, 2019 in European Patent Application No. 16828447.9.

* cited by examiner

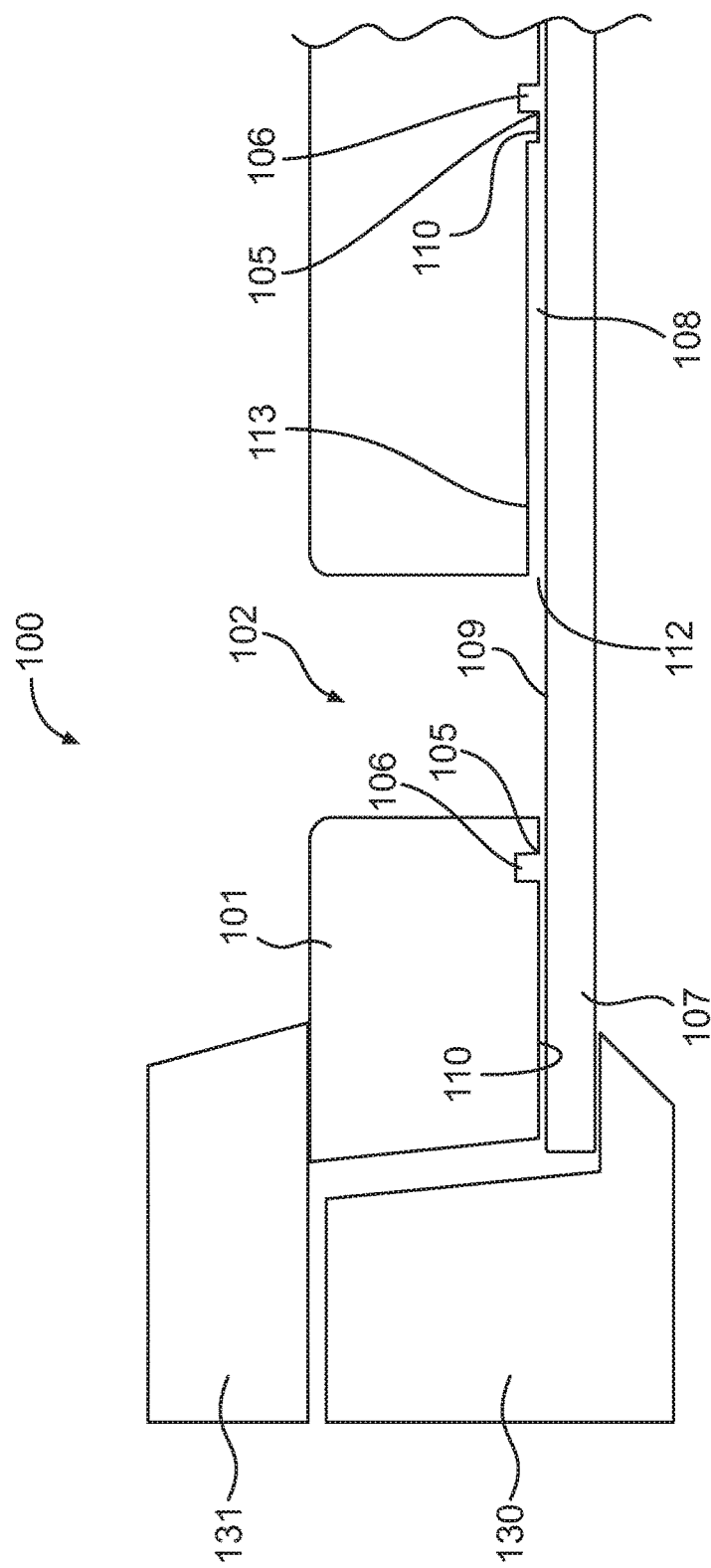
FIG. 1.1

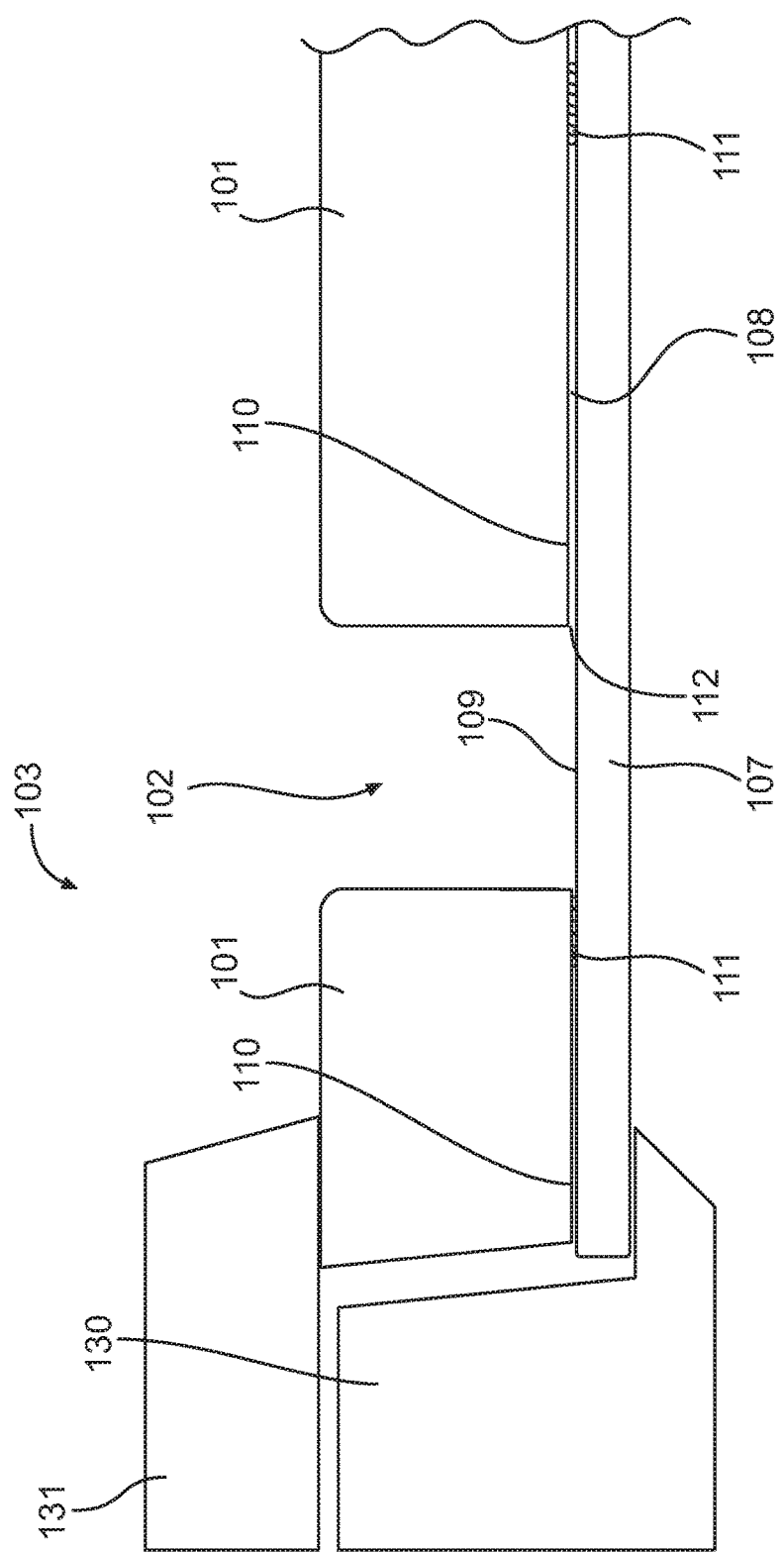
FIG. 1.2

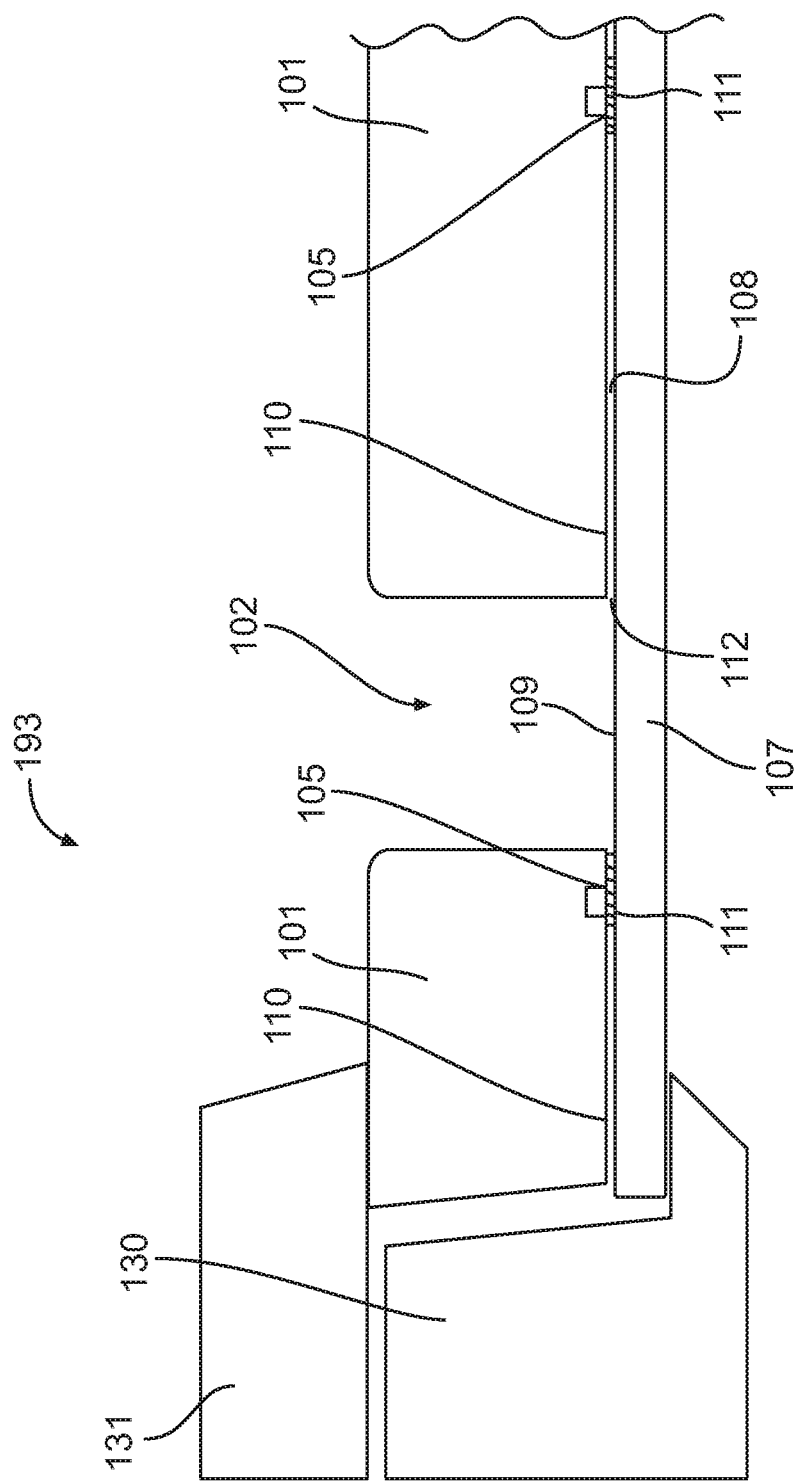
FIG. 1.3

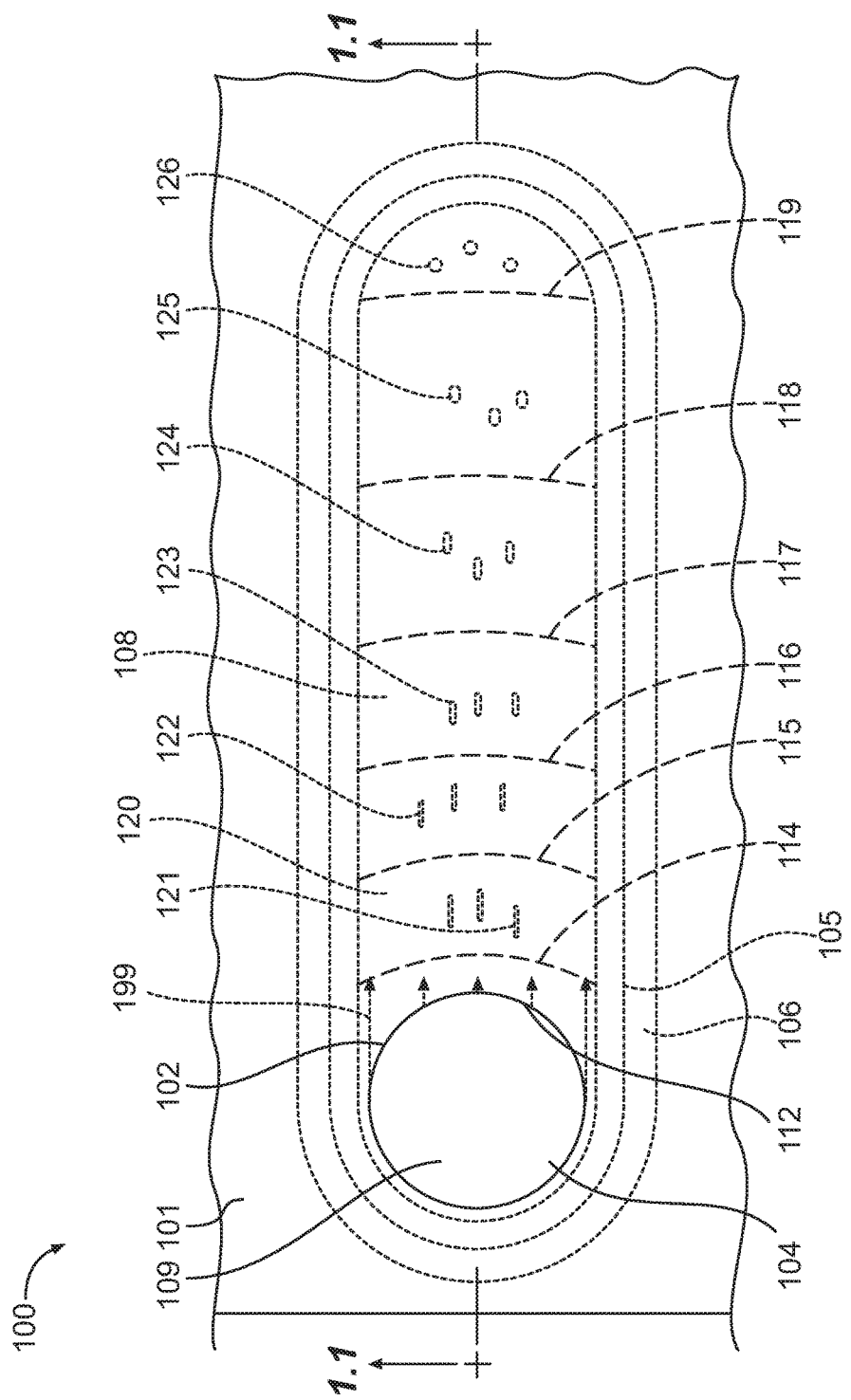
FIG. 1.4

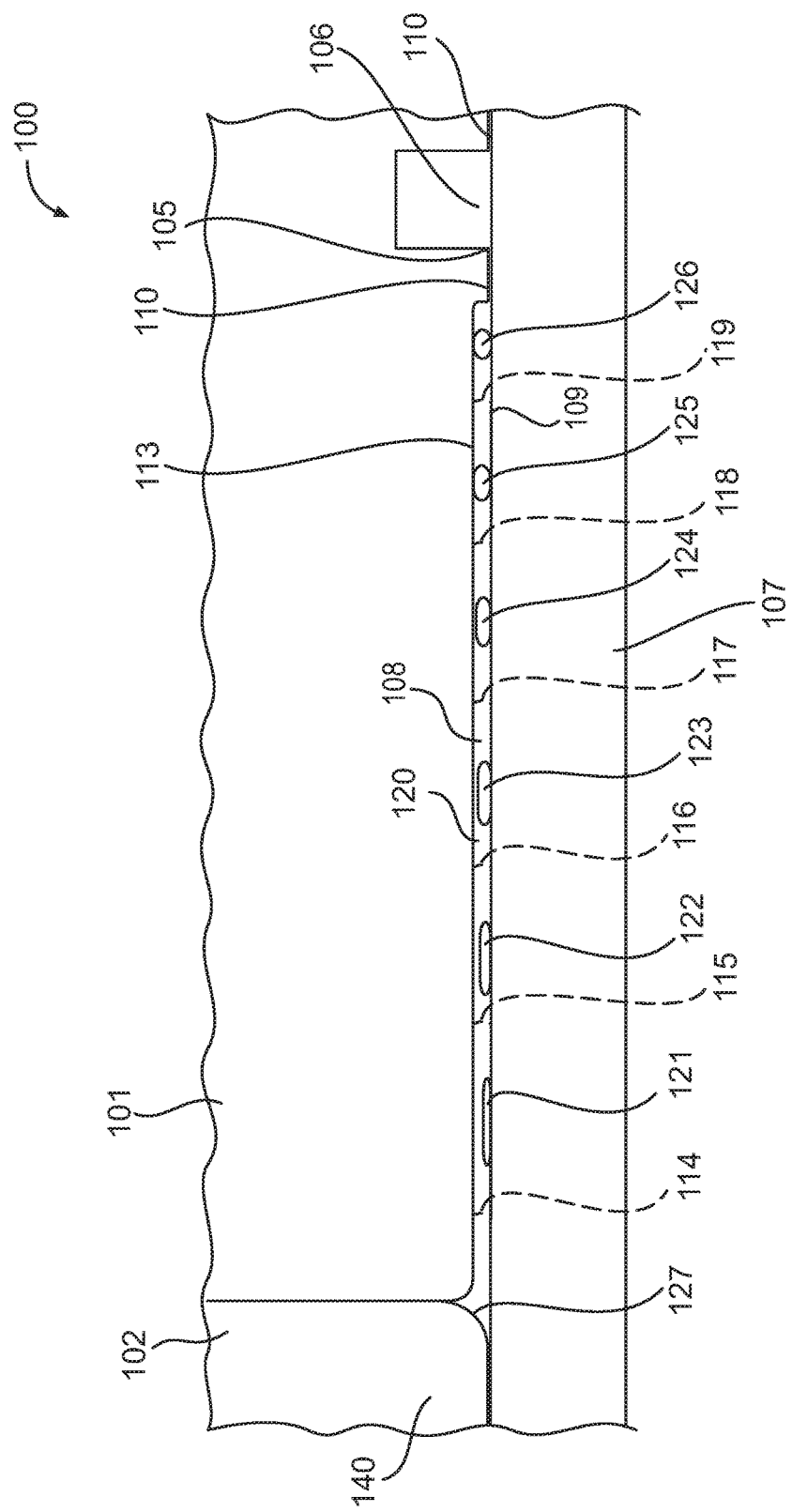
FIG. 1.5

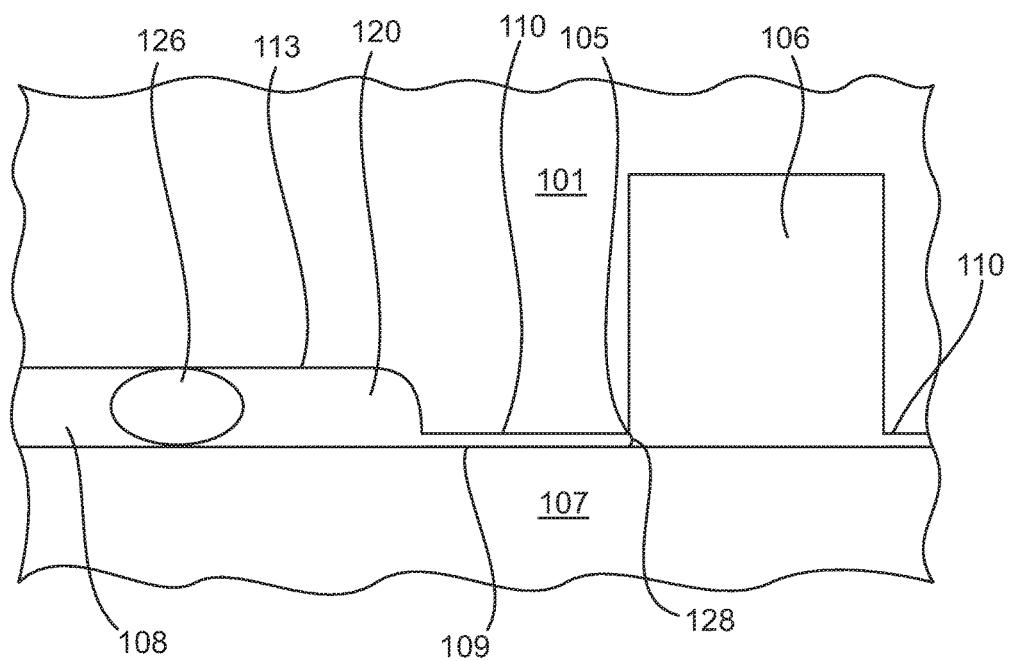
FIG. 1.6

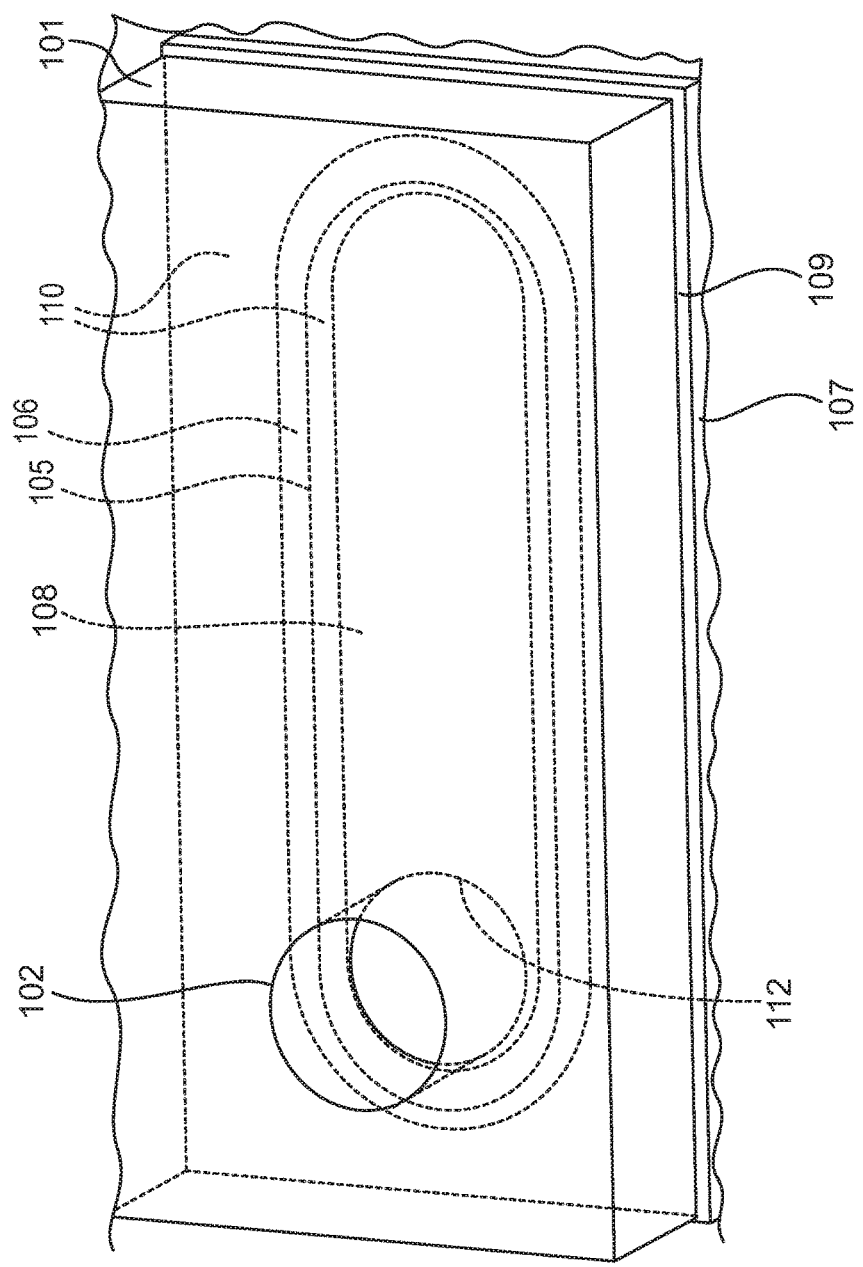
FIG. 1.7

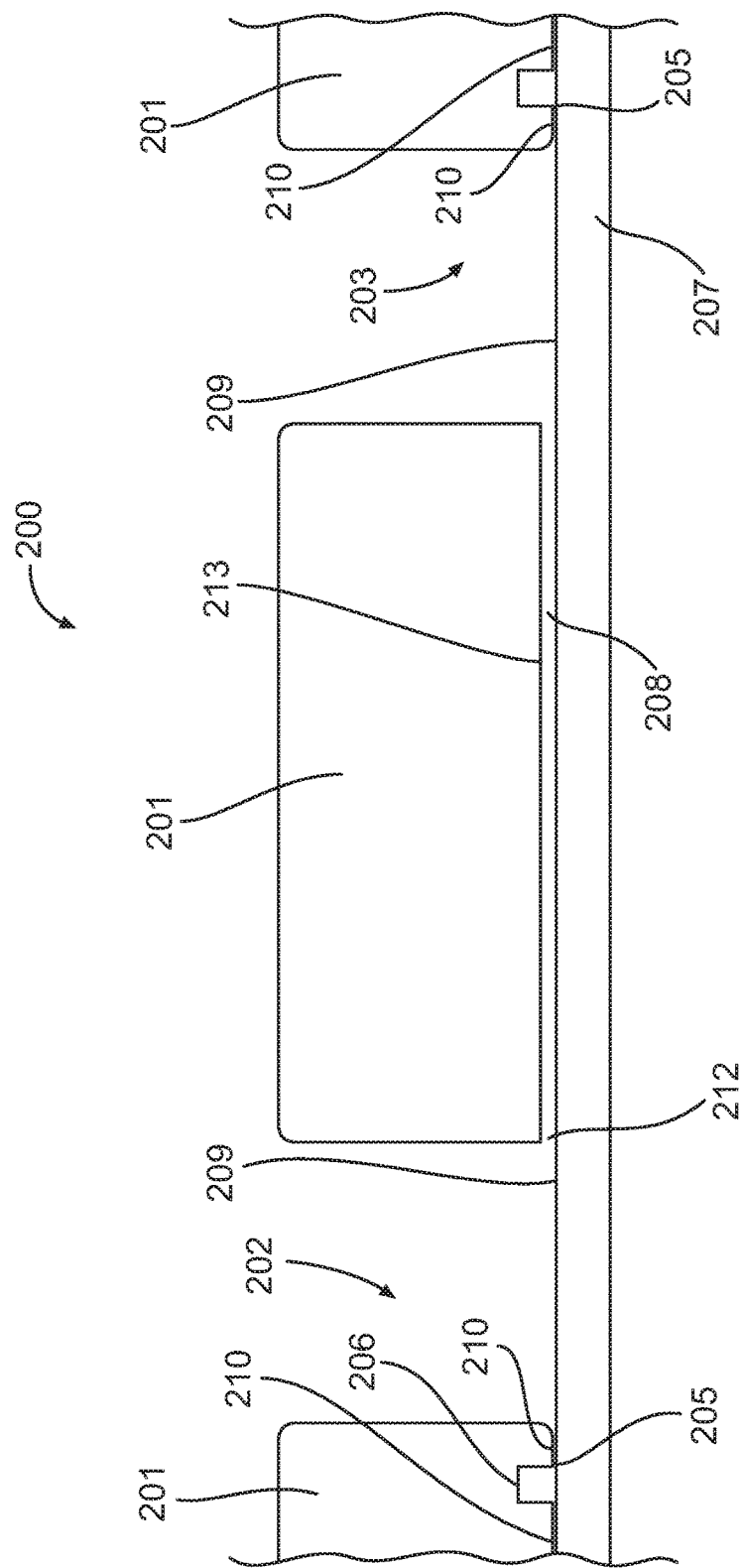
FIG. 2.1

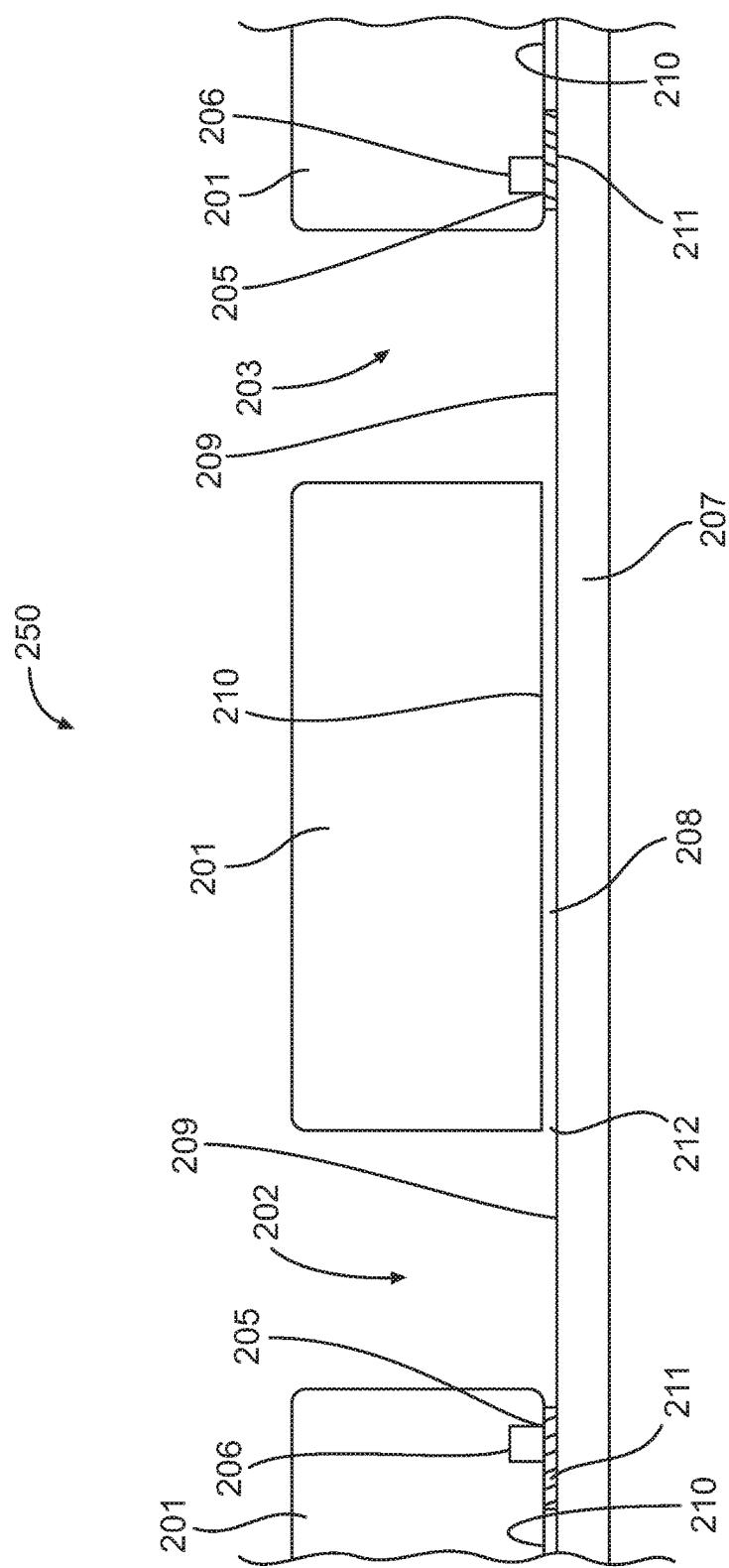
FIG. 2.2

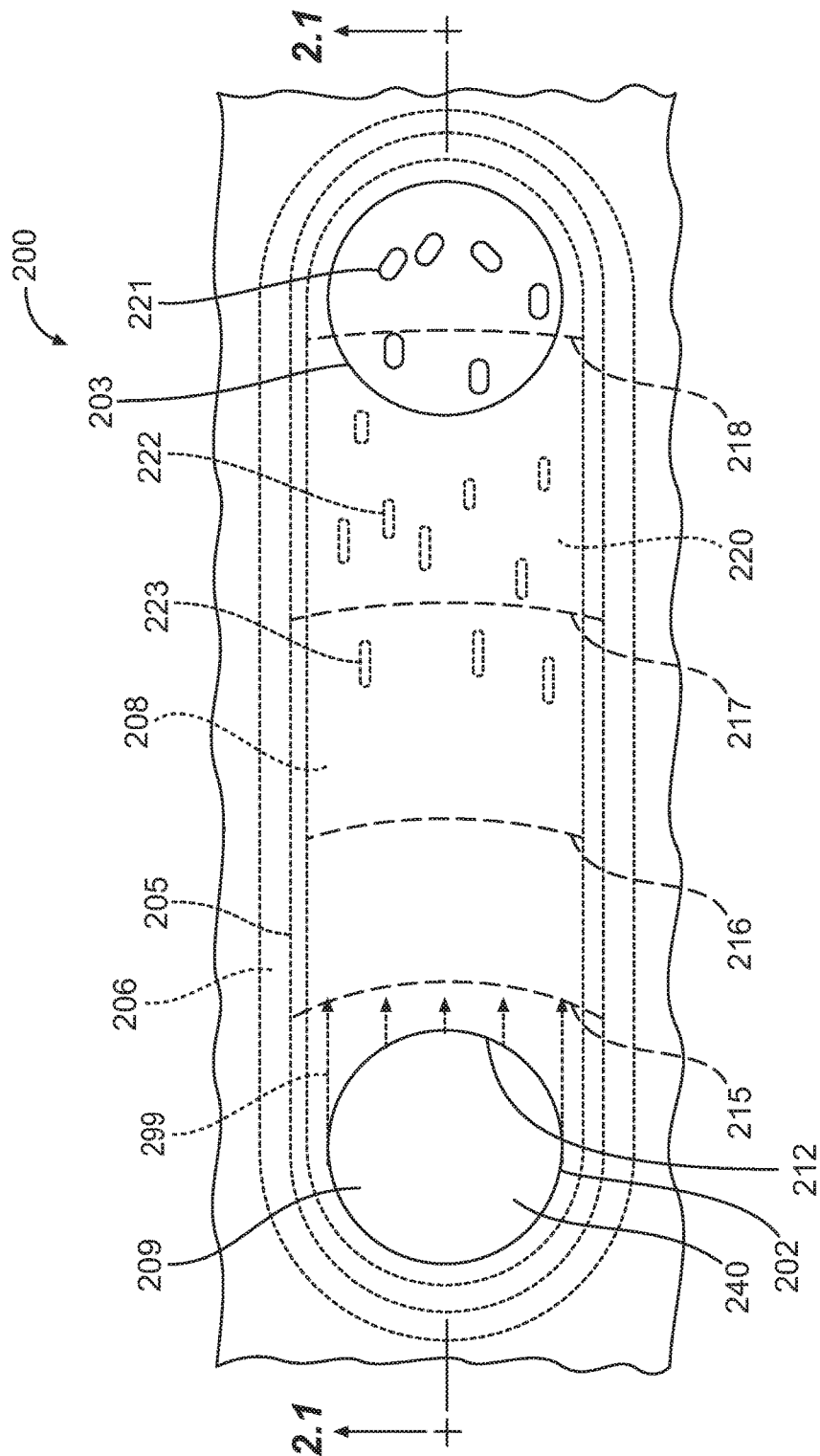
FIG. 2.3

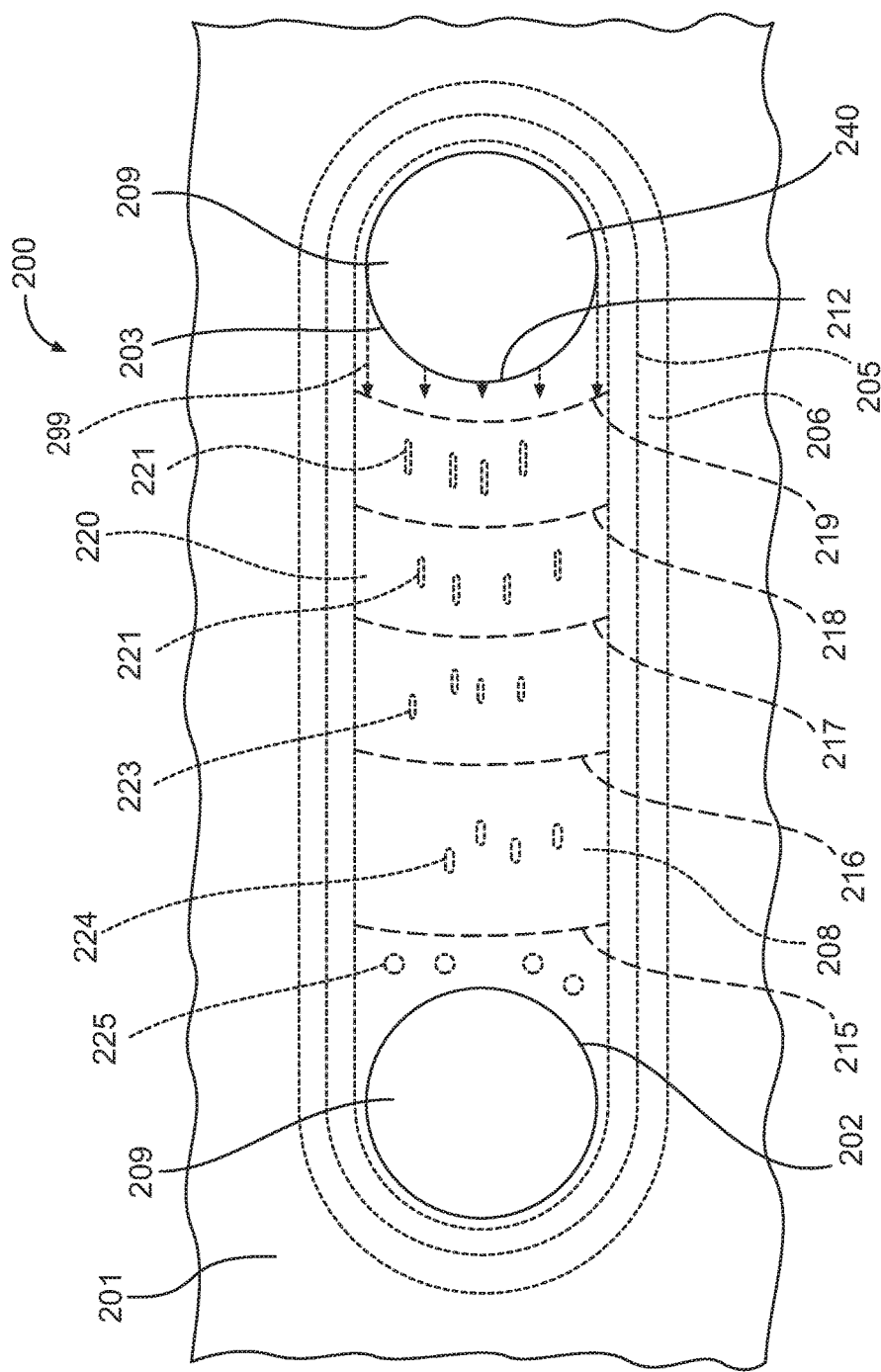
FIG. 2.4

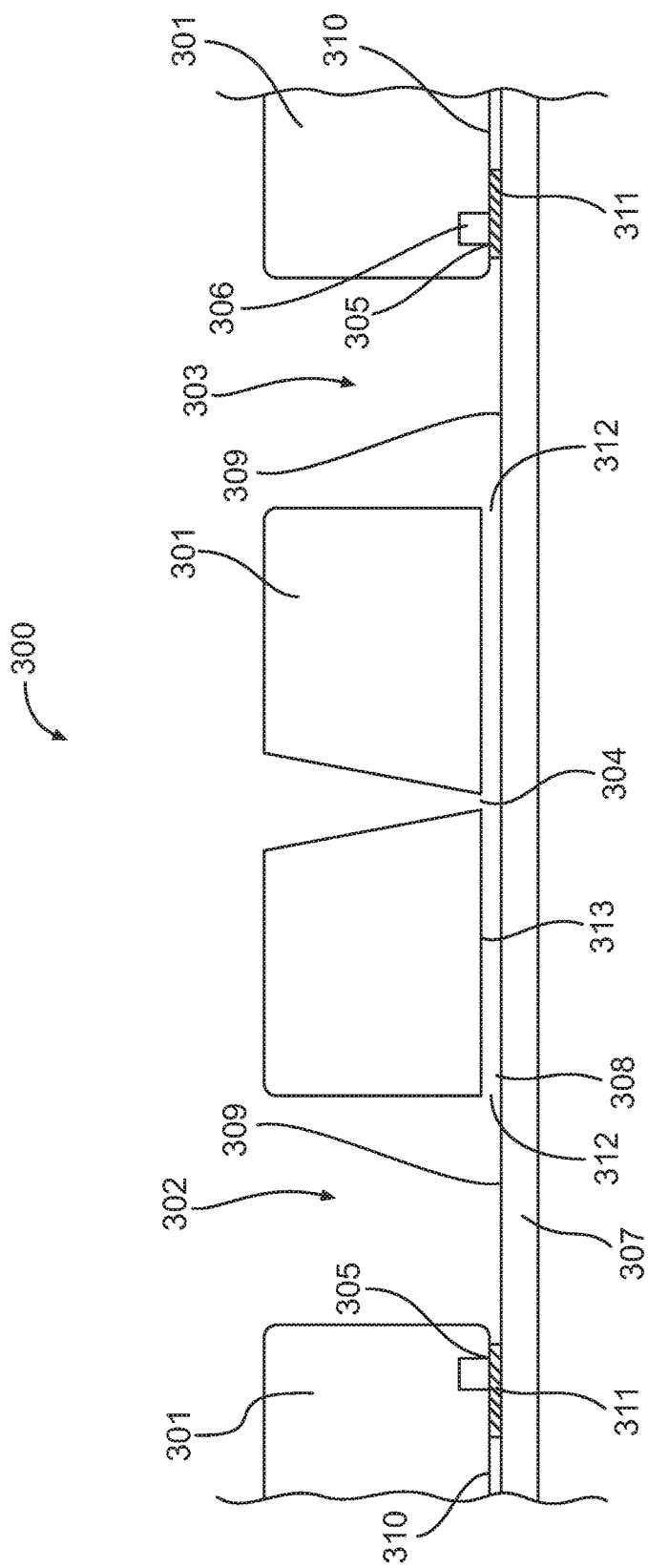
FIG. 3.1

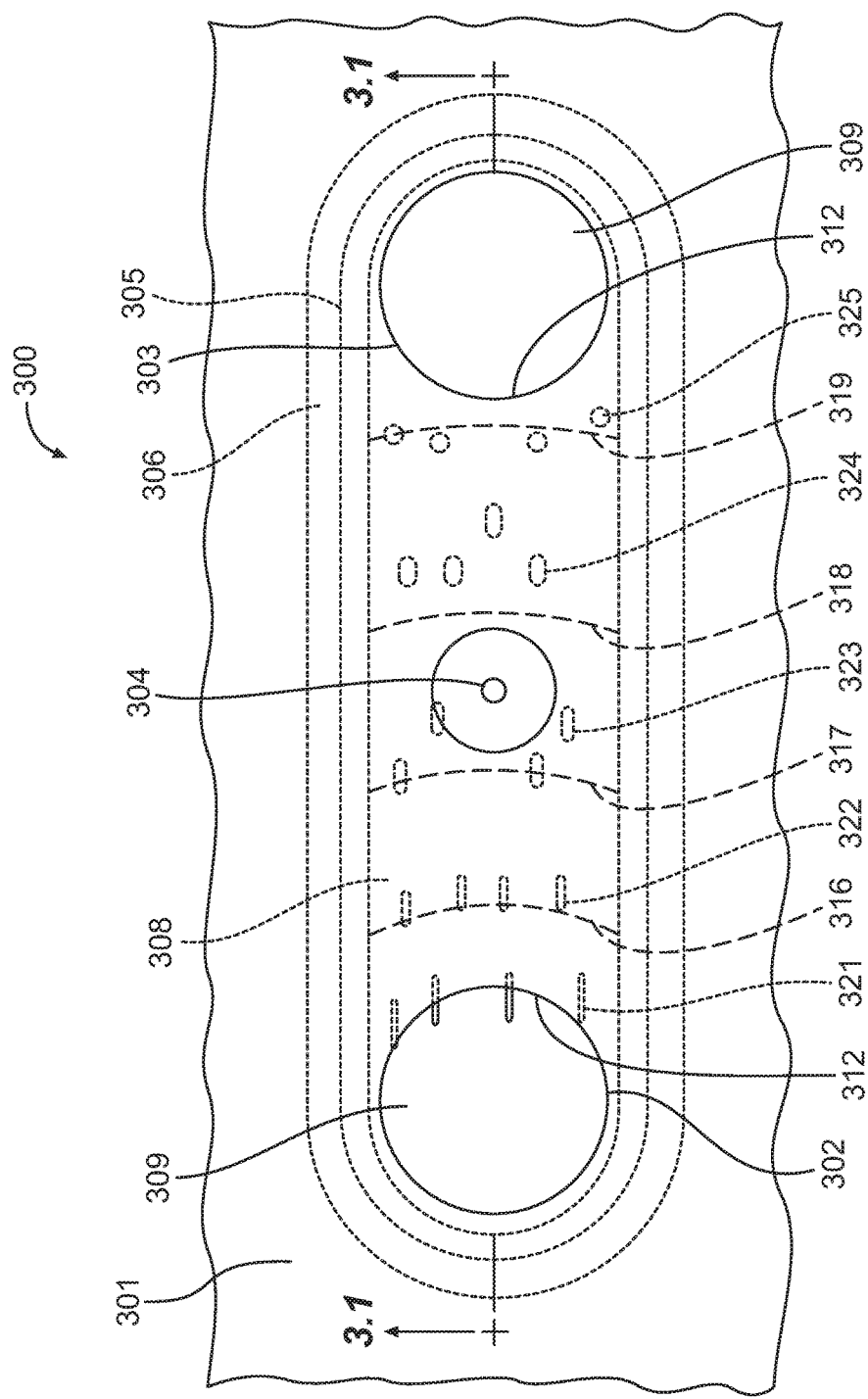

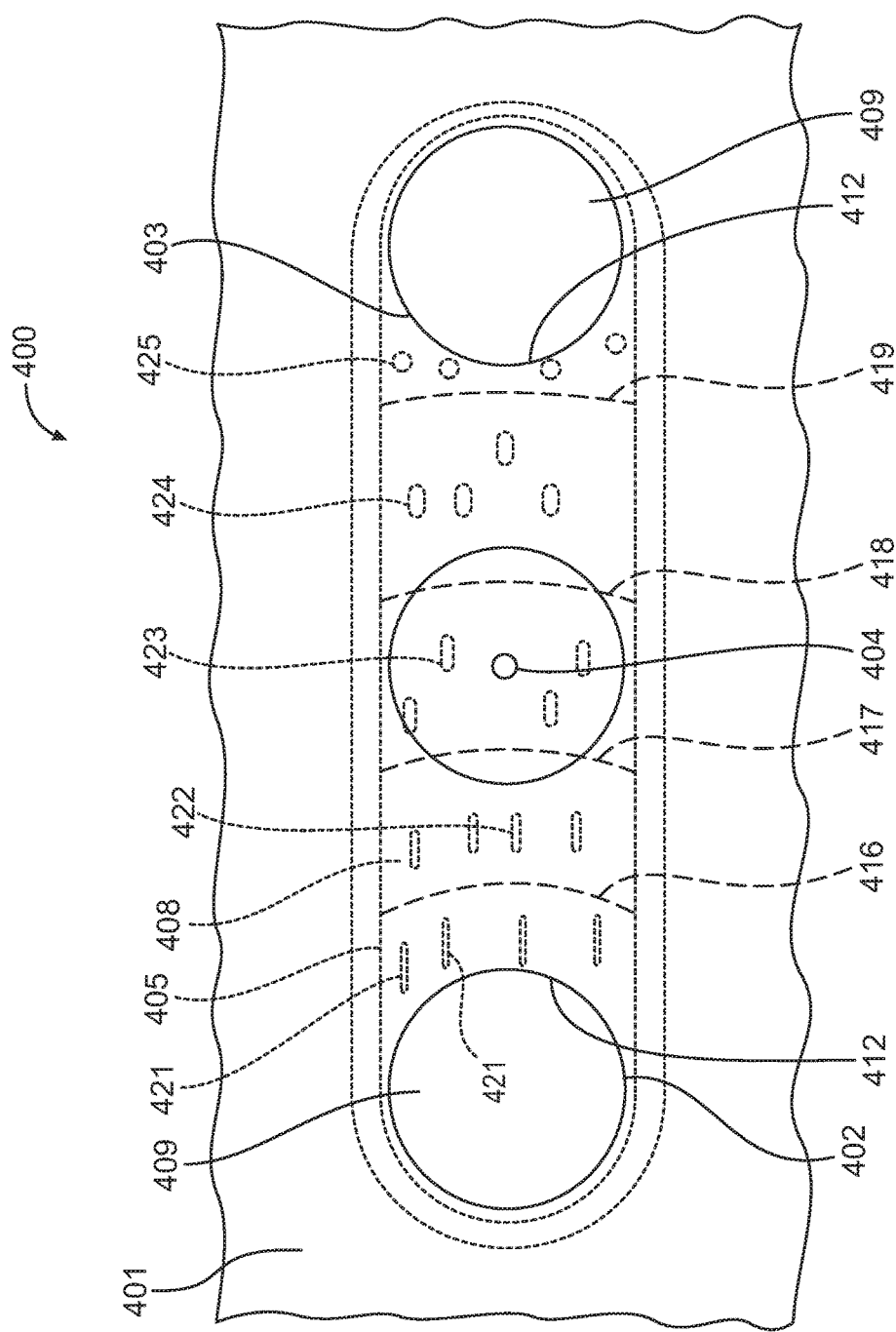
FIG. 4.1

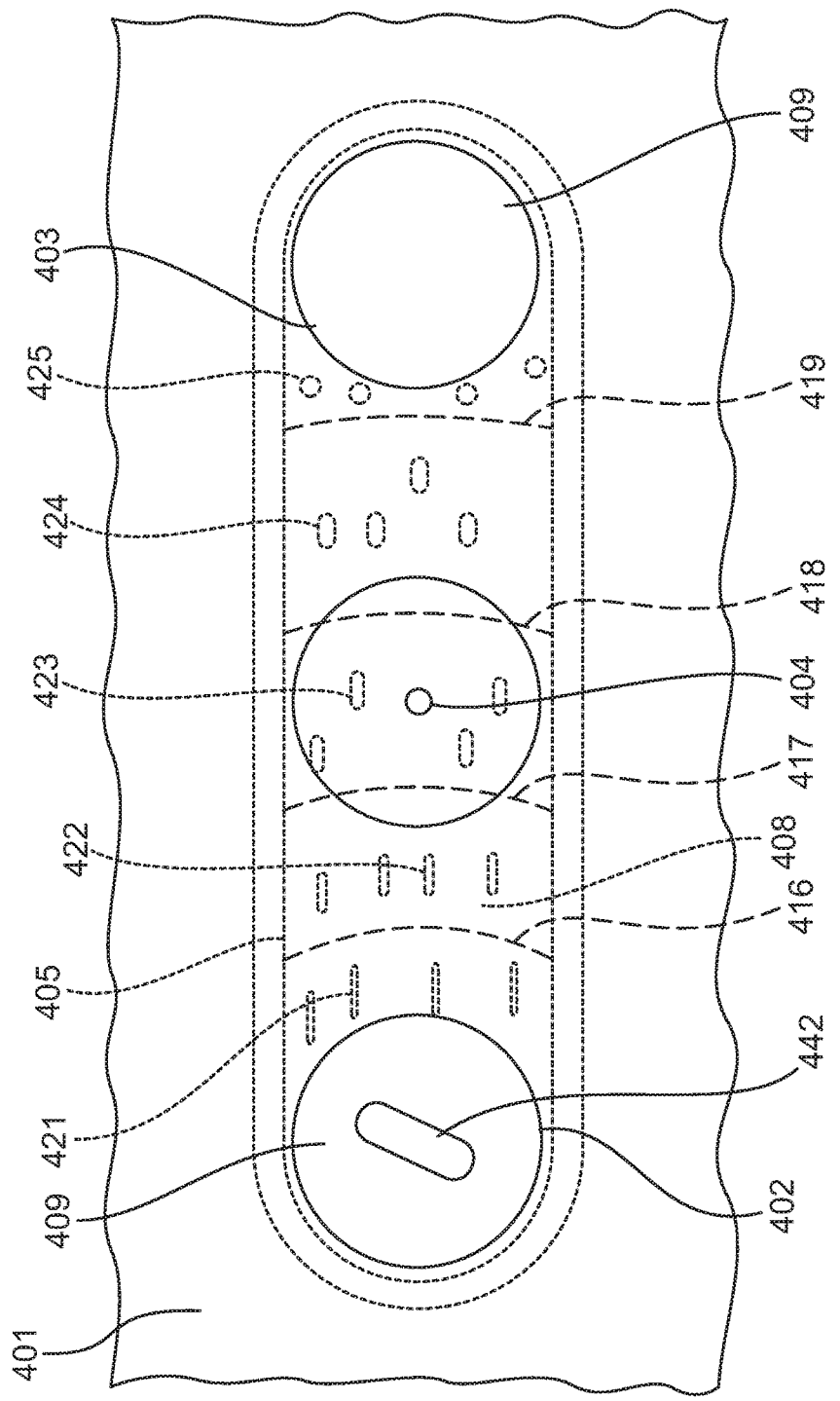
FIG. 4.2

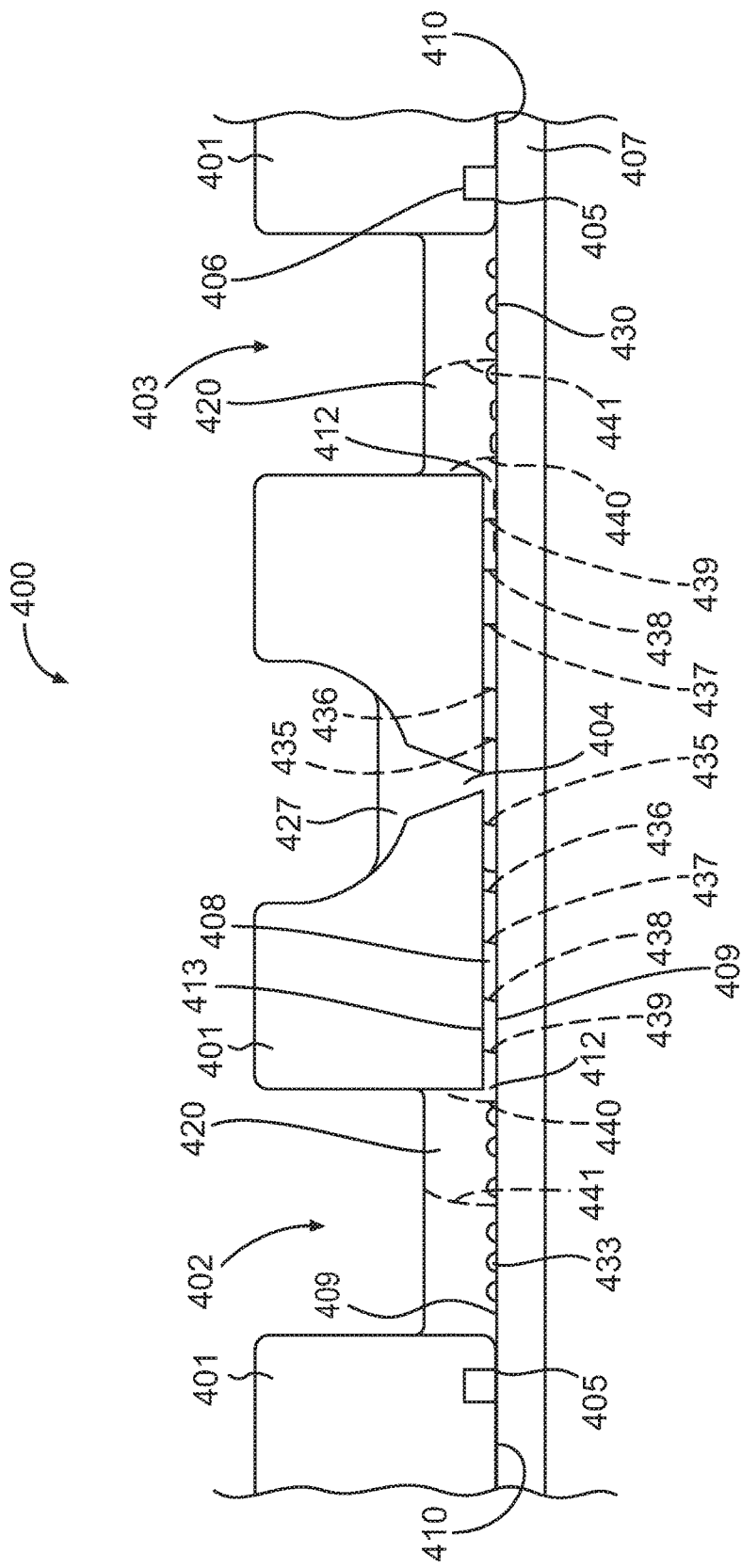
FIG. 4.3

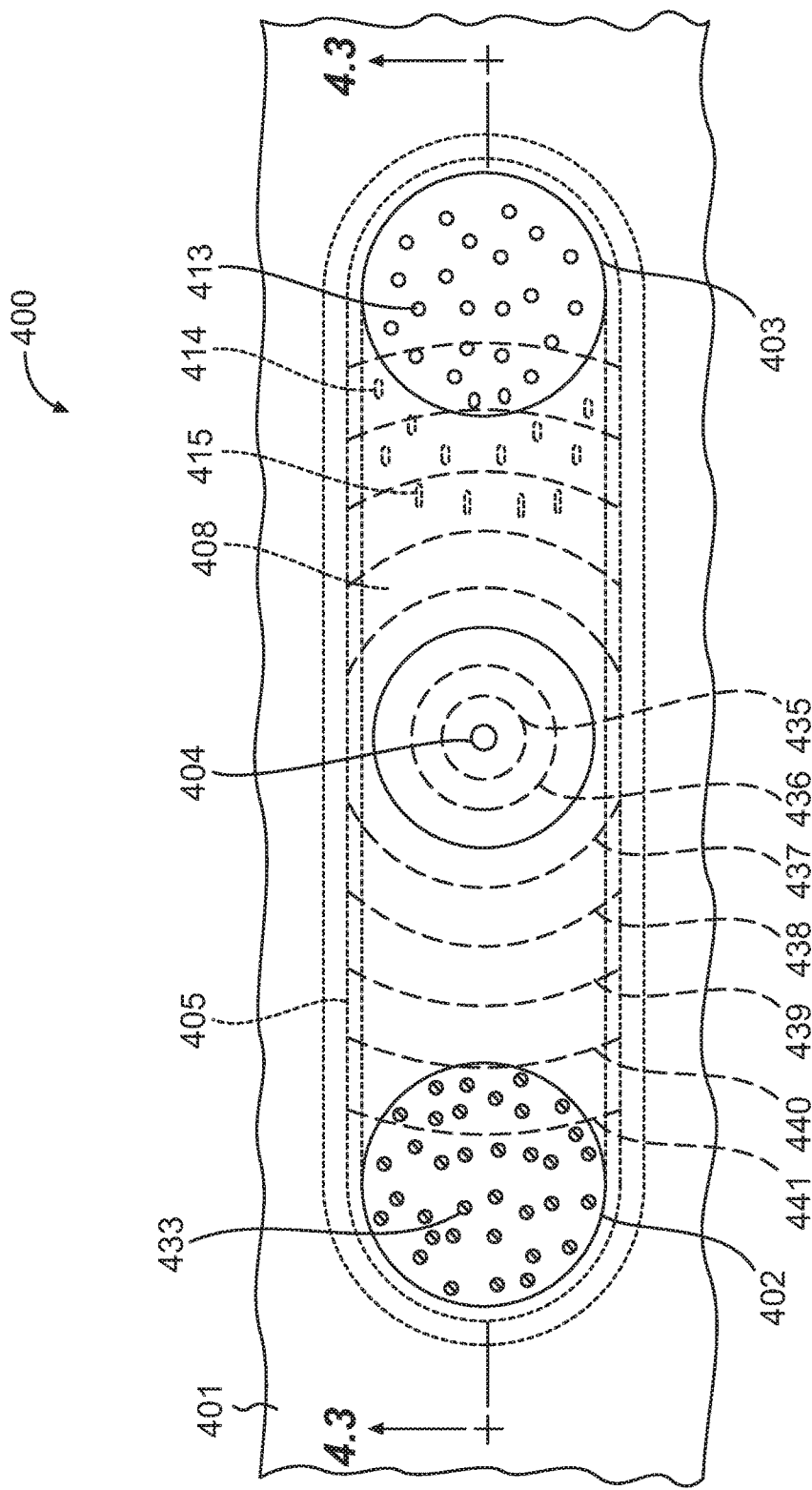
FIG. 4.4

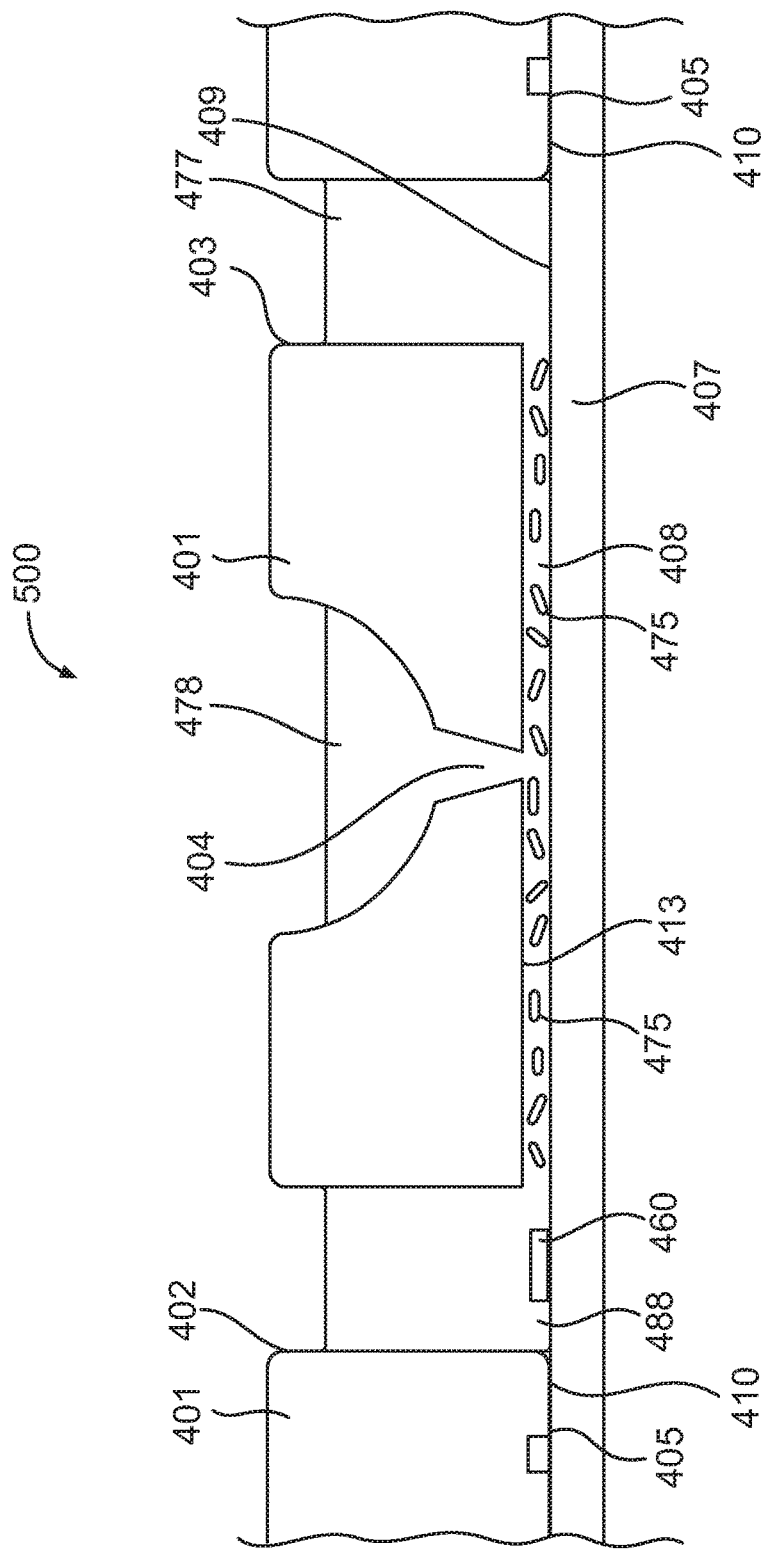
FIG. 4.5

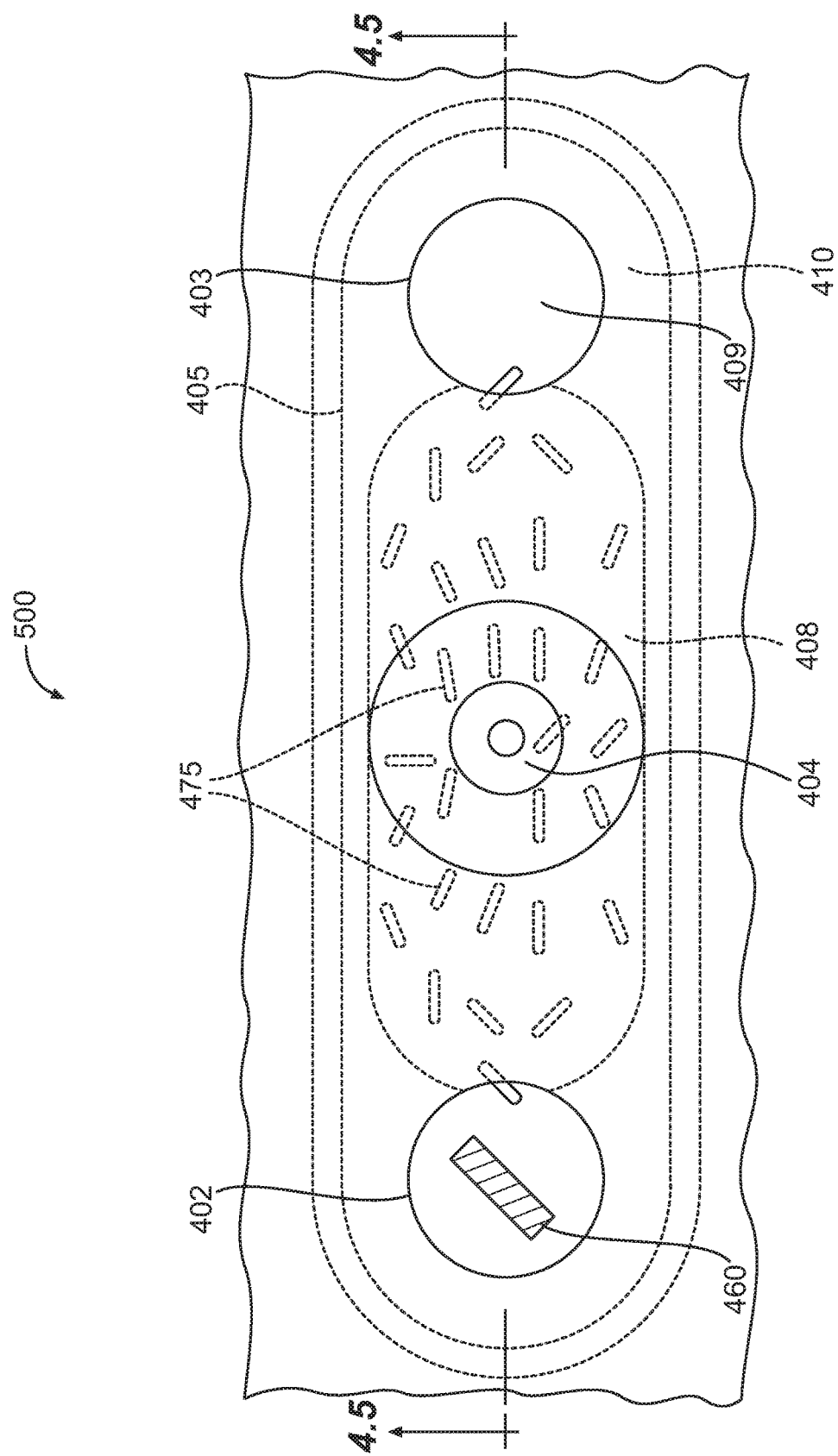
FIG. 4.6

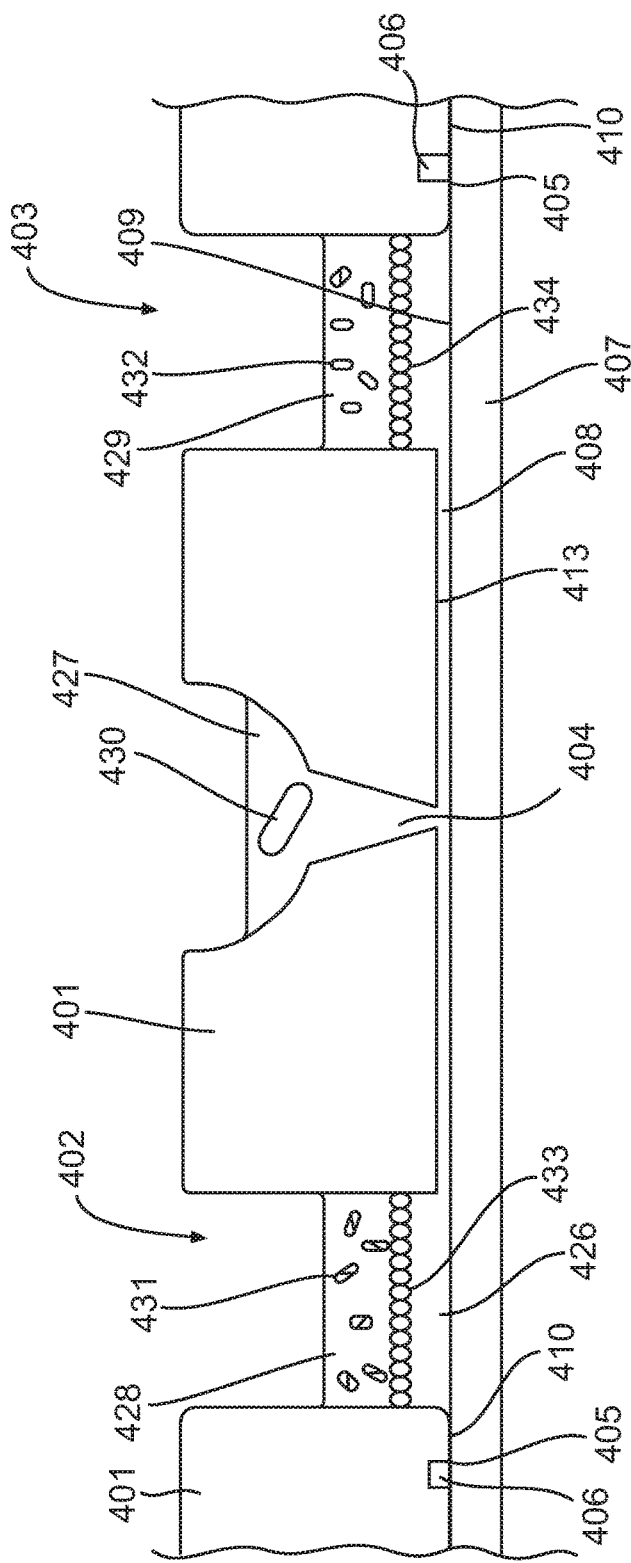
FIG. 4.7

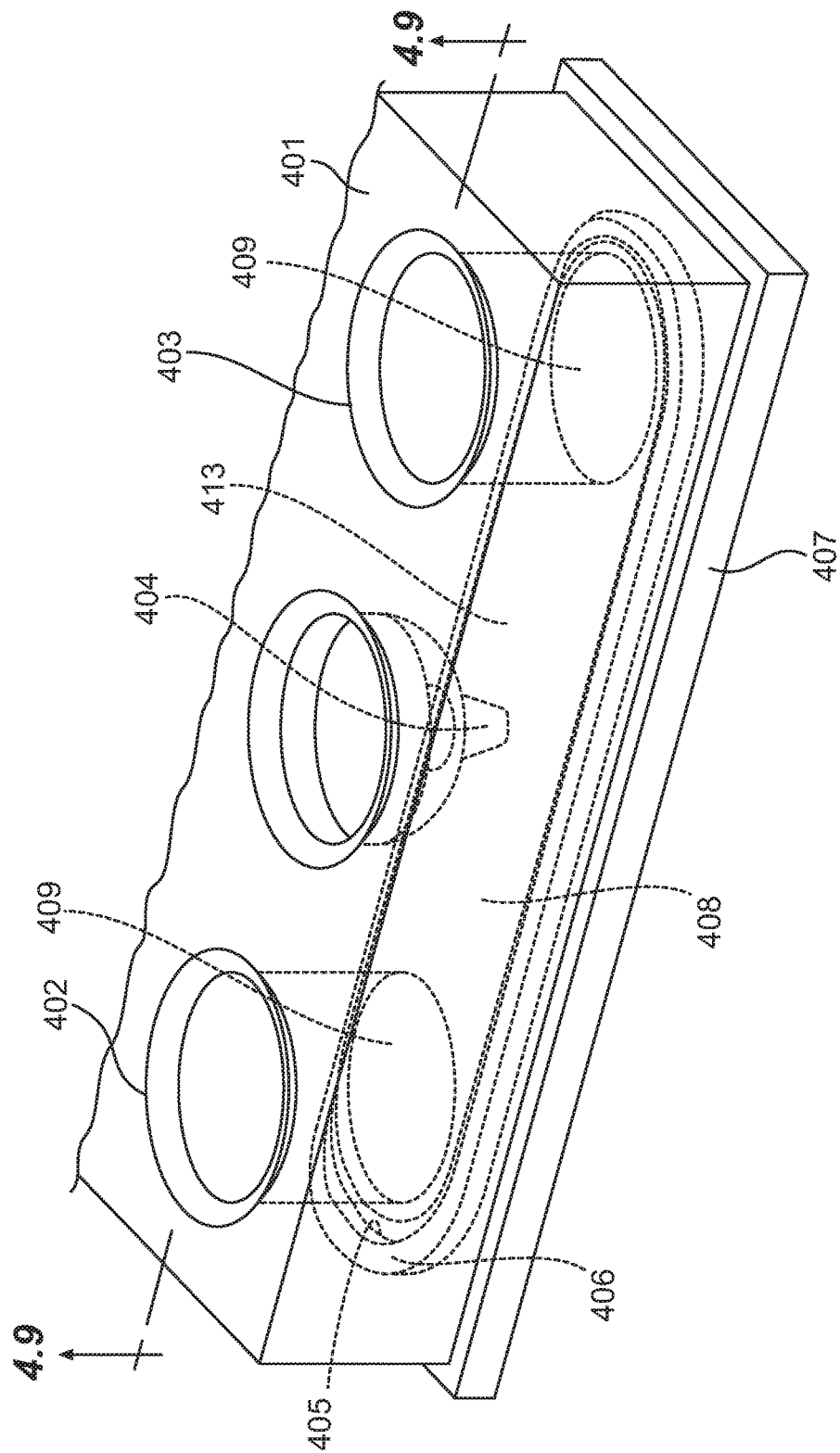
FIG. 4.8

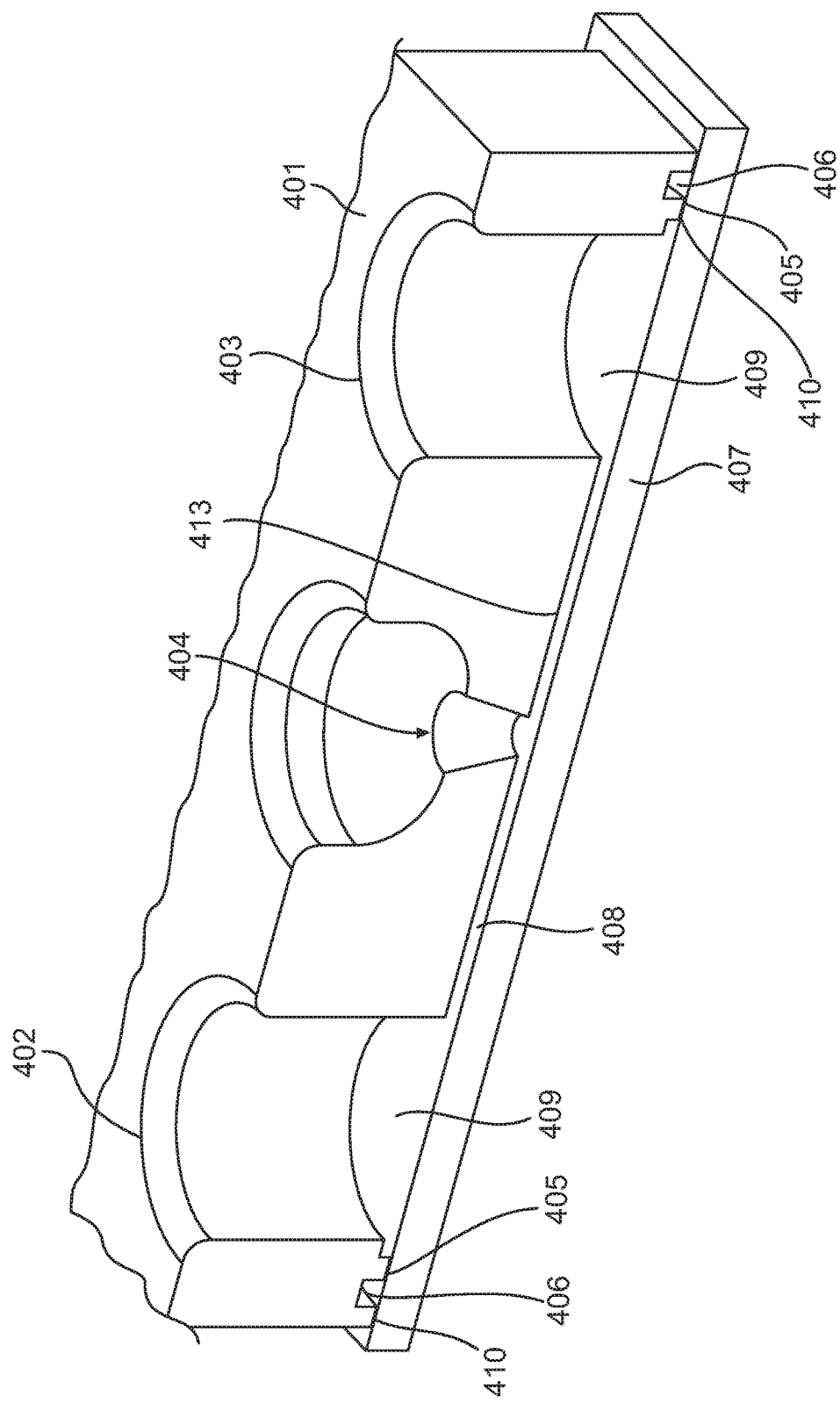
FIG. 4.9

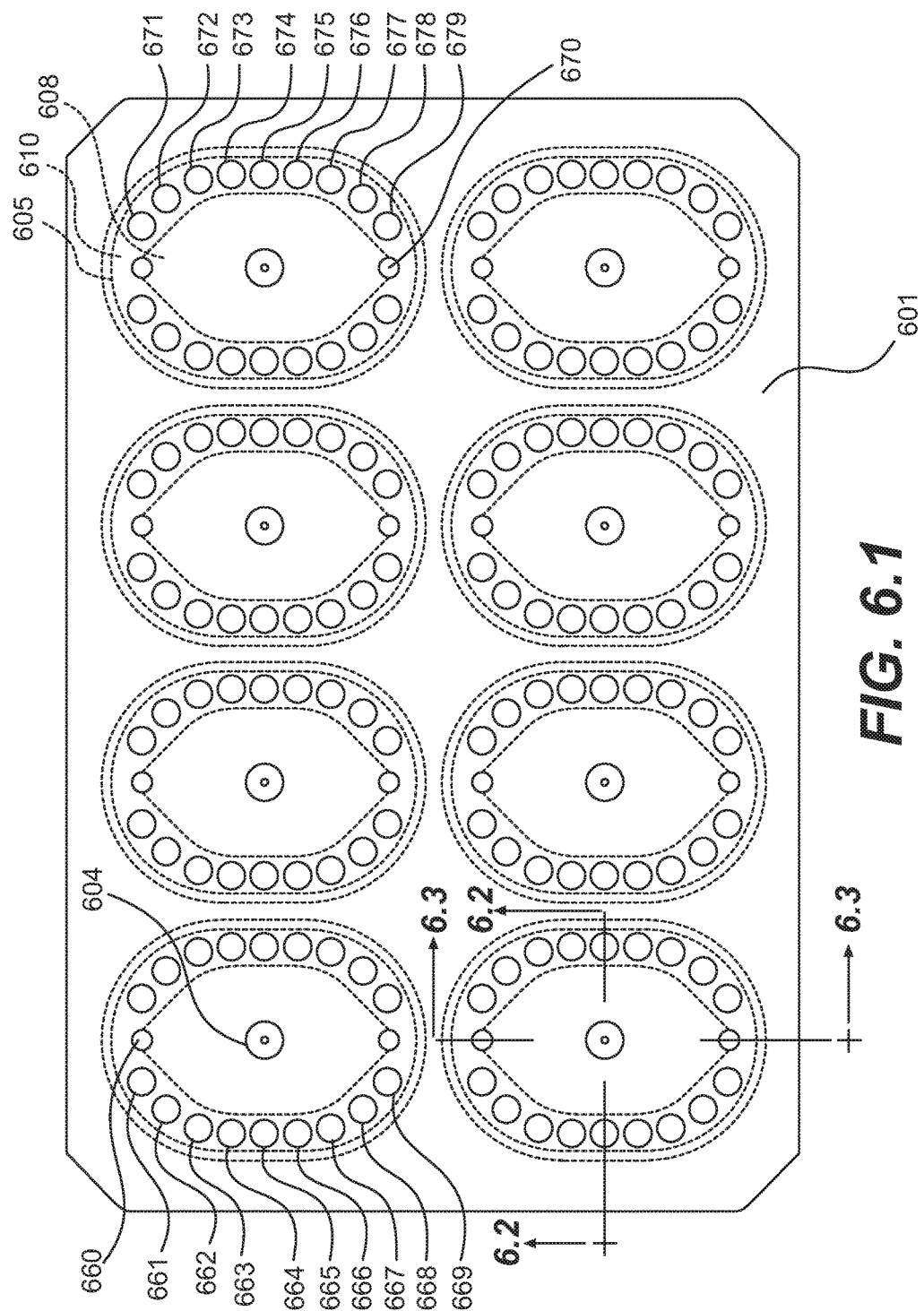
FIG. 6.1

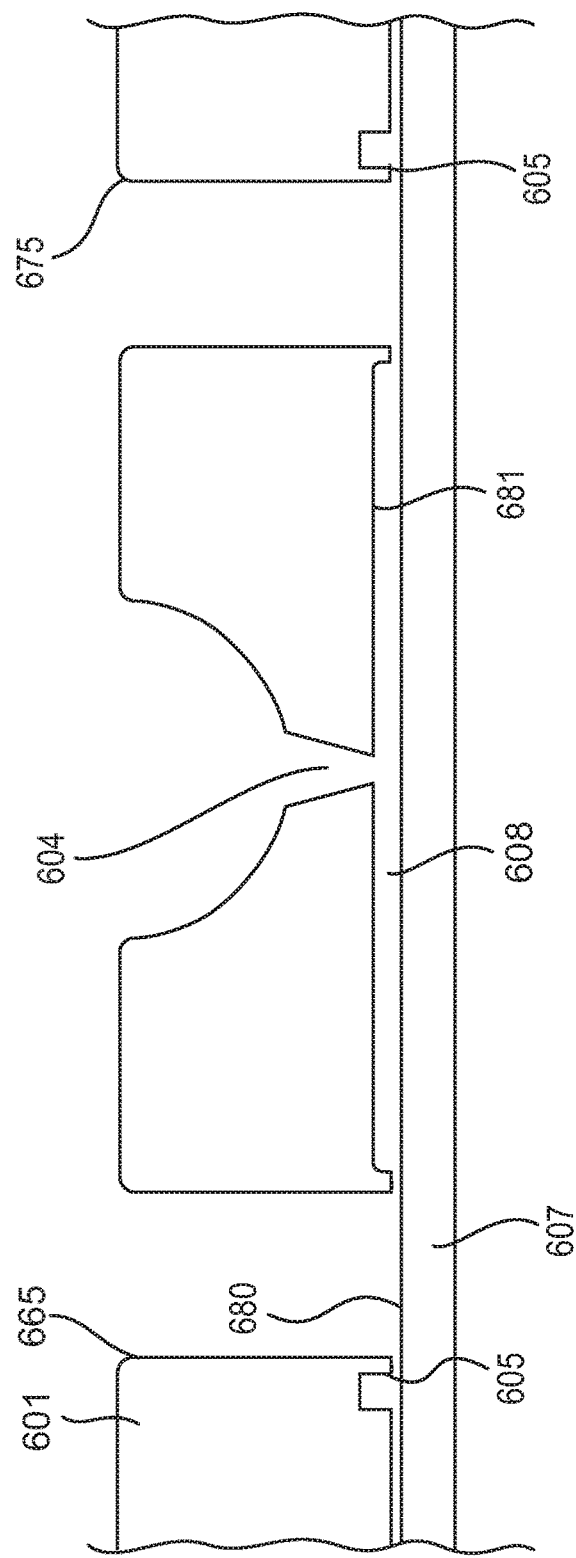
FIG. 6.2

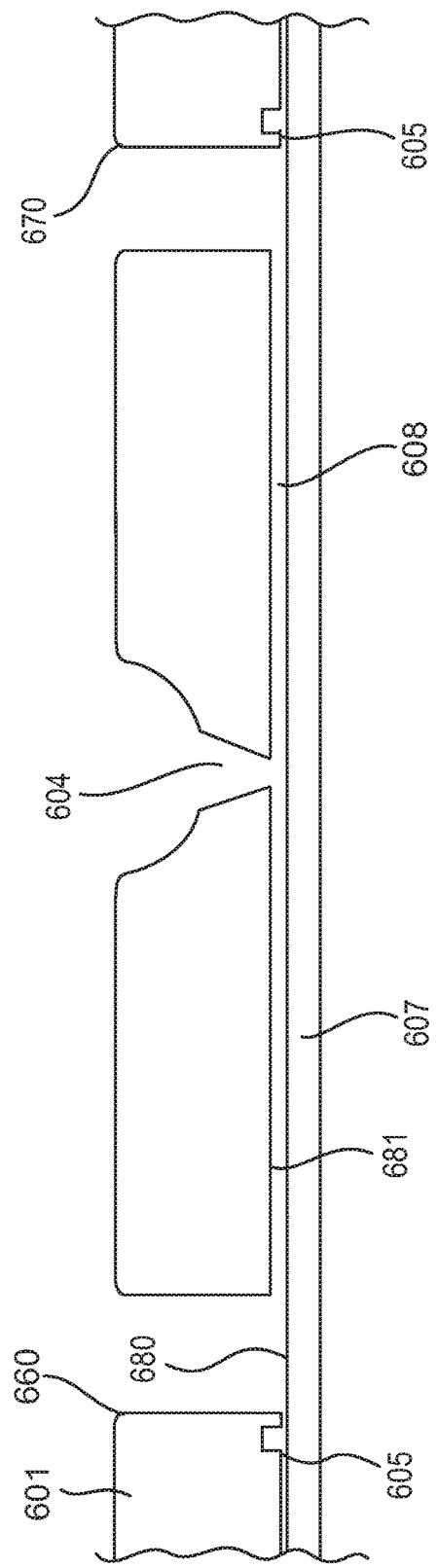
FIG. 6.3

ASSAY APPARATUS AND METHODS

This application claims the benefit of U.S. Provisional Application No. 62/194,888, filed Jul. 21, 2015, which is herein incorporated by reference in its entirety.

BACKGROUND

Field

The present embodiments relate to methods and apparatus for high content screening (HCS) and high throughput screening (HTS) and basic (low throughput) research. In particular, the present embodiments relate to cell activity assays (CAA) that prevent cell activity or inhibit cell activity, or involve chemotaxis, migration, angiogenesis, growth, proliferation, and other cell activity based on, for example, morphology, shape, and movement of cells. The present embodiments also relate to cell activity assays involving changes internal to cells such as differentiation, alteration of metabolic rate, and movement of molecules within a cell initiated by activation of receptors in the cell membrane. The present embodiments also relate to cell activity assays involving the interaction of cells in response to various chemical environments, and the interaction of different cell types with one another. The present embodiments also relate to assays involving the penetration of cell layers by chemical compounds or other entities, and to assays for ascertaining the diffusion rate of members of a compound library through various confluent cell layers, e.g., endothelial or epithelial cell layers.

Background

Pharmaceutical companies expend considerable resources on researching and developing drug therapies. The research and development process, from conception to eventual approval by the Food and Drug Administration (FDA), can last several years. Thus, in the initial stages, it is highly desirable to quickly rule out unusable chemical substances and focus efforts on effective substances. In particular, there is a need for rapidly and accurately assessing whether and to what extent cell activity is affected by compounds.

In addition, pharmaceutical companies and research institutions may desire flexible assay platforms that can be conveniently customized for particular studies or applications. Budget-conscious researchers may appreciate assay platforms that can be customized and assembled for a first study, and then disassembled, sterilized, and customized and re-assembled for a second different study.

SUMMARY

Embodiments provide apparatus and methods for rapidly and accurately assessing whether and to what extent cell activity is affected by compounds that make contact with a living cell's membrane. The present embodiments may perform this assessment with minimal cost in cells, reagents, assay platforms, and other disposables, and with very low coefficients of variability, thus allowing primary screening of large compound libraries without using duplicate or triplicate sites for each compound. The present embodiments may provide an assay apparatus for HCS, HTS, CBHTS, and cell based screening, as well as basic research in cell activity. The apparatus and methods of the present embodiments facilitate cell activity assays. In particular, the present embodiments may provide means for assessing whether compounds from a compound library can induce cell activity, e.g., chemotaxis. In contrast to the prior art, the present embodiments may allow for the determination of cell activity by detecting changes in cells that occur well before a cell could migrate through a membrane. These changes may include, for example, cell orientation, internal morphological changes, temperature variations, molecular movement within the cell, and electromagnetic changes—in short, any change in cells that can be detected.

Pharmaceutical companies expend considerable resources on researching and developing drug therapies. The research and development process, from conception to eventual approval by the Food and Drug Administration (FDA), can last several years. Thus, in the initial stages, it is highly desirable to quickly rule out unusable chemical substances and focus efforts on effective substances. In developing drug therapies, pharmaceutical companies typically start with a vast library of chemicals. From this library, a large number of the chemicals may have the potential to therapeutically act on the cells associated with the disease or ailment for which the drug is being developed. Determining which chemicals affect the cells is therefore an important step in drug development.

Chemotaxis is the directional movement (migration) of biological cells or organisms in response to concentration gradients of chemicals. Invasion is the movement (migration) of cells into or through a barrier. Tumor invasion is such action initiated by cancer cells into or through biological tissue in vivo, or into or through extra cellular matrix proteins, e.g., collagen or matrigel, or into or through barriers made of other substances, in vitro. Angiogenesis is the migration and formation of capillary blood vessels by endothelial cells. Growth is the increase in the size, form, or complexity of cells. Proliferation is the growth of cells by cell division. Differentiation is the process by which cells change from a less specialized to a more specialized state usually associated with different functional roles and the expression of new and different traits.

Interaction of cells is the alteration of cell behavior such as movement, invasion, angiogenesis, growth, proliferation, or differentiation in response to the presence and action of nearby cells of the same or different type. The movement of compounds and structures within cells is another kind of cell activity that can be of interest in drug discovery. For example, powerful optical detection systems may track the movement of florescent compounds (e.g., proteins) within the cell. These detection systems may be used to observe many different changes in internal cell activities in response to contact by compounds from a library with the cell's membrane or receptors. These activities and similar activities are referred to herein collectively as "cell activity," and the apparatus employed to perform the assays are referred to herein as "cell activity assay apparatus."

One kind of single-site cell activity assay apparatus referred to variously in the literature as "chemotaxis chambers," "Boyden chambers," "Boyden chemotaxis chambers," and "blind-well chambers," may have two compartments separated by a membrane, with one or both of the compartments open to air. Multi-site apparatus, often referred to as "multi-well chemotaxis chambers" or "multi-well Boyden chambers," may have the same basic site structure but have multiple sites. See, e.g., U.S. Pat. Nos. 5,210,021 and 5,302,515, which are herein incorporated by reference in their entirety.

Assays employing this kind of apparatus may pipette cells suspended in media into the upper compartments, and pipette chemotactic factors and controls into the bottom compartments. The chemotactic factors may be used in various dilutions to get a dose-response curve. The controls are generally of three kinds: (a) negative, when the same media that is used to suspend the cells is also used below the membrane; (b) chemokinetic, when a chemotactic factor is placed at the same concentration in the media with the cells and in the well on the opposite side of the membrane; and (c) positive, when a known chemoattractant is placed in the bottom wells. Chemokinetic controls may allow the user to distinguish heightened random activity of the cells, due to contact with the chemotactic factor, from directional response in a concentration gradient of that chemotactic factor.

Cell activity assay apparatus may also be used to measure the response of cells of different origins, e.g., immune cells obtained from patients suffering from diseases, to a compound with known chemotactic activity. In this case, the cells in question are interrogated by both a negative control and a known chemotactic factor to see if the differential response is depressed or normal. Traditionally, chemotactic activity has been measured by establishing a stable concentration gradient in the cell activity assay apparatus, incubating it for a predetermined time, and then counting the cells that have migrated through the membrane (or into the membrane). A comparison is then made between the activity of the cells in a concentration gradient of the chemotactic factor being tested, and the activity of the cells in the absence of the concentration gradient.

In one type of cell activity assay apparatus and method, the chemotactic response may be measured by physically counting the number of cells on the membrane surface closest to the chamber containing the chemical agent. An example of this type of cell activity assay apparatus is described in U.S. Pat. No. 5,210,021, which is herein incorporated by reference. One method of obtaining quantitative data is to remove the membrane from the cell activity assay apparatus, remove the cells from the membrane surface closest to the chamber containing the original cell suspension, fix and stain the remaining cells, and then observe and count the stained cells under a microscope. Because of the time and expense associated with examining the entire membrane, only representative areas of the membrane may be counted, which may render results less accurate than would otherwise be the case if the entire membrane were examined and counted.

Cell activity assays using a disposable ninety-six well microplate format, for example, the ChemoTx™ System (available from Neuro Probe, Inc., Gaithersburg, Md.), may be amenable to different methods of quantification of results. The manual staining and counting method described above can be used, but is not recommended due to the time involved. A preferred method is to centrifuge the microplate with the filter attached such that the cells that have migrated through the filter are deposited onto the bottom of the lower wells. The cells may then be stained with MTT, MTS (available from Promega, Madison, Wis.), or a similar dye, and then read in a standard automated laboratory densitometric reader (sometimes referred to as an Elisa plate reader).

Another method of obtaining quantitative data with this type of apparatus is to dye the cells with a fluorescent material, e.g., Calcein AM (available from Molecular Probes, Eugene, Oreg.), centrifuge the migrated cells into the microplate, and count cells with an automatic fluorescence plate reader (e.g., Cytofluor available from PE Biosystems, Foster City, Calif.; Victor2 available from EG&G Wallac, Gaithersburg, Md.; or fmax available from Molecular Devices, Sunnyvale, Calif.). The automatic plate reader excites the fluorescent dye in the migrated cells with one wavelength of light and reads the light emitted at a second wavelength. Alternatively, the cells that have not migrated may be removed from the top of each site, and the plate with the framed membrane attached may be read in the automatic fluorescent plate reader without spinning the cells into the plate, thereby counting the cells that have fallen off the filter into the lower well as well as those on the bottom of the membrane and in the pores of the membrane.

As described above, past efforts at measuring chemotactic activity have focused on measuring or counting cells that have passed through a long, tortuous path, such as through a filter or thick membrane. Because of their dependence on cell migration, these techniques may present significant drawbacks. First, the cells must migrate a considerable distance through the media to the chemotactic factor, which may add substantial time to the assay. Second, to obtain desirable (low) coefficients of variation, a relatively large number of cells is needed to calculate percentages of migration. Consequently, these assays demand large volumes of compound from a compound library, which are not always readily available. Third, in migration assays that count the number or percentage of cells that have passed through a filter, the results provide quantitative data, but not kinetic data. In addition, the results provide no information about the cells that have not passed through the filter.

In contrast to migration assays, the present embodiments may more quickly determine cell activity by detecting changes in the cells that occur well before migration. Those changes may include, for example, cell orientation, internal morphological changes, temperature variations, molecular movement within the cell, and electromagnetic changes.

To provide that early detection, embodiments may provide a side source from which a test compound solution diffuses into a cell suspension media and contacts cells. A side source may be an opening positioned to the side of a test site, which extends substantially across the width of the test site, and from which a test compound solution diffuses in a substantially linear fashion into a cell suspension media (e.g., moving substantially in a line or as a substantially linear "front"), away from the side source, and across the test site, and contacts cells within the test site. Since the side source extends substantially across the width of the test site, diffusion from the side source on one side of the test site may be substantially linear across the test site. In embodiments, the side source extends across substantially the entire width of the test site. For example, a test site may have an elongated shape (e.g., oval shape) when viewed from a plan view, and the side source may extend across nearly the entire width of the test site, as described in embodiments herein.

The present embodiments may also provide an apparatus having a side source, a point source, or both, from which a test compound solution may diffuse into a cell suspension media and contact cells therein. The term "point" as used herein in the expression "point source" is not intended to be a geometric term, but a relative term referring to a center area from which a compound diffuses concentrically. Since the area of a point source in this usage is relatively small with respect to the area of the entire site (e.g., less than 10% of area of the entire site), diffusion from the center area into the rest of the site is experimentally equivalent to diffusion from a point. As an example, the concentric diffusion may be readily observed from a top or bottom view of a site, with progressive rings extending outwardly from the point source in circles or in portions of circles (e. g., semicircles or quarter circles) depending on the configuration of the site and the location of the point source. Examples of point source diffusion are described in U.S. Pat. Nos. 7,547,525, 8,129,175, and 8,486,655, which are herein incorporated by reference in their entirety.

In some of the present embodiments, a side source may be one type of a point source, based on the size and location of the point source relative to the configuration of a test site. As described above, diffusion from a point source may be in portions of circles depending on the configuration of the site and the location of the point source. Thus, for example, a side source may be provided by a point source located at a side of a test site that is long and narrow relative to the size of a point source. In that configuration, the partial-circle diffusion may be substantially linear along the long and narrow test site.

The present embodiments may control the rate of this diffusion so that cell activity can be progressively monitored. In one aspect of the present embodiments, the rate of diffusion may be gradual so that the cell activity caused by the test compound solution occurs in stages as the test compound solution diffuses farther from the side source, so that periodic readings of the site may detect such progressive changes. Embodiments may control the rate of diffusion using, for example, a gel layer occluding an opening through a top plate, a gel containing test compound solution, a sintered material containing test compound solution, a frozen test compound solution, a dried or freeze-dried test compound solution, and combinations thereof. One embodiment may provide a method for determining whether a test compound solution induces cell activity comprising placing the test compound solution in contact with a cell suspension media containing cells, diffusing the test compound solution into the cell suspension media from a side source, a point source, or both, and detecting activity in the cells with respect to their distance from the side source, point source, or both. Detecting activity in the cells may involve detecting activity in a first group of the cells proximate to the side source, point source, or both, and detecting activity in a second group of the cells farther from the side source, point source, or both, than the first group.

Another embodiment may provide a cell activity assay apparatus that includes a top and bottom plate, and an opening through the top plate, through which cell suspension media may be disposed on the top side of the bottom plate proximate to a side aperture leading to a cavity between the two plates, into which the suspension may spread. The test compound solution may then be disposed on the top side of the bottom plate next to a side aperture leading to the cavity between the two plates. In this configuration, the test compound solution contacts the cell suspension media within or proximate to the side aperture, and diffuses into the cell suspension media, creating a concentration gradient emanating from the side aperture into the cell suspension media.

In one embodiment, there may be multiple openings to the cavity, one of which is a small hole, and the concentration gradient may extend concentrically from this opening. The cells nearest the opening may be contacted first by the test compound solution. Subsequently, as the test compound solution diffuses farther from the opening, the other cells may be contacted radially outward in stages. If the cells are responsive to the test compound solution, the progressive diffusion may provide progressive cell activity that, when monitored with suitable detection means, yields both quantitative and kinetic (e.g., changes in the cells as a function of time) data on cell activity.

An embodiment may provide a method for performing a cell activity assay using the apparatus described above. According to this method, a cell suspension may be deposited onto the top side of a bottom plate proximate to a side aperture leading to a cavity formed by the top surface of the bottom plate and a bottom surface of a top plate, into which cavity the suspension may spread. The apparatus may then be incubated, which may allow cells to settle out of the cell suspension and adhere to the top side of the bottom plate, leaving cells adhered to the top side of the bottom plate and cell suspension media covering the cells. Optionally, the apparatus may then be "read" to provide a baseline reading of the cells' morphology and activity. "Read" in this context may involve acquiring a high resolution picture (digital or otherwise) with, e.g., a high content screening detection instrument. The test compound solution may then be deposited on the top surface of the bottom plate proximate to a side aperture leading to a cavity—formed by the top surface of the bottom plate and a bottom surface of a top plate—that is occupied by the cell suspension. The test compound solution may be deposited, for example, by pipetting onto the top side of the bottom plate, by a pin applicator, by projecting the test compound solution down onto the top surface of the bottom plate, or by other appropriate means. With the test compound solution deposited, the test compound solution may be in contact with the cell suspension media at the side aperture of the cavity. With this contact, the test compound solution may begin diffusing into the cell suspension media. The site may then be read periodically to observe the effect of the test compound solution on the cells as this diffusion progresses. These readings detect, for example, cell elongation and orientation, other morphological changes, temperature changes, movement of molecules and structures within a cell, and electromagnetic changes. Detecting morphological changes involves, for example, examining the aspect ratio (length to width ratio) of the cells. Detecting cell orientation involves, for example, examining the orientation of the aspect ratio in relation to the side aperture from which the test compound solution is diffusing.

Alternatively, the apparatus described above may also be used first in assay development to determine the optimal time to perform a single detection step, and then in the screening stage (which is typically the expensive stage in time and materials) with a single detection or reading step. The assay development stage may use multiple detection steps—it may create a "movie" of the cells responding through time—which demonstrates and records the kinetics of the process. From this data, an optimal time may be determined for performing a single detection or reading step in the actual screen. The single detection step may be at a time when the test compound has diffused across the site or part way across the site.

Thus, there will be many geometrically distinct subpopulations of cells in the site at that time: at one end, proximate to the side source of the test compound, there is a subpopulation that has been exposed to the test compound the longest duration and at the other end, farthest from the side source of the diffusion, is a subpopulation that has been exposed the least duration. Typically, the optimal time to acquire the single detection step may be when the subpopulation at one end of the site shows no change in cell activity, the subpopulation at the other end of the test site (which has been exposed the longest) shows the largest alteration in its activity, and the subpopulations in between show a continuum of change in cell activity from a lot to a little to none at the end of the site farthest from the side source.

Furthermore, the exposed subpopulation has been exposed progressively—those closer to the side source exposed longer than those farther away. Thus, even though there is a single detection step, the activity, non-activity, and extent of activity of the cells will express the kinetics of the situation. In this manner, the present embodiments can detect activity in the cells with respect to their distance from the side source.

ABBREVIATIONS & DEFINITIONS

1. "High throughput screening" is herein abbreviated to "HTS."
2. "Cell-based high throughput screening" is herein abbreviated to "CBHTS."
3. "High Content Screening" is herein abbreviated to "HCS."
4. "Nanometer" is herein abbreviated to "nm."
5. "Microliters" is herein abbreviated to "ul."
6. "Micrograms" is herein abbreviated to "ug."
7. "Test compound solution" as used herein may refer to a solution composed of a compound of interest to a researcher, for example, a compound from a compound library, dissolved in water, cell culture media, dimethyl sulfoxide (DMSO), other appropriate media, or a combination thereof.
8. "Cell suspension media" as used herein may refer to a media or fluid capable of suspending cells.
9. "Cell suspension" as used herein may refer to a solution containing cells suspended in a cell suspension media.
10. "Point source" as used herein may refer to a center area from which a chemical compound diffuses concentrically.
11. "Side source" as used herein may refer to a side aperture or opening of a cavity in an assay platform from which an aqueous solution can enter and a chemical compound solution can diffuse. It may be a type of point source.
12. "Mechanical hydrophobic barrier" as used herein may refer to a physical feature of an assay apparatus (e.g., a groove in the bottom of a plate with sharp right angles) that, when held against a flat surface of a second plate, creates a barrier to aqueous solutions and prevents their passing without significant hydrostatic pressure being applied.
13. "Chemical hydrophobic barrier" as used herein may refer to a chemical feature of an assay apparatus, e.g., a chemical compound applied to a plate, or a film incorporating a chemical compound that is held against a (flat top) surface of a plate, that creates a barrier to aqueous solutions and prevents their passing without significant hydrostatic pressure being applied.
14. "Read" as used herein may refer to the capture of data from the sites of a cell activity assay apparatus, which may include the acquisition of images, digital or otherwise, from each site of the cell activity assay apparatus.

Other systems, methods, features, and advantages of the embodiments will be, or will become, apparent to one of ordinary skill in the art upon examination of the following figures and detailed description. It is intended that all such additional systems, methods, features, and advantages be included within this description and this summary, be within the scope of the embodiments, and be protected by the claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. In addition, in the figures, like reference numerals designate corresponding apparatus parts throughout the different views.

FIG. 1.1 is a schematic diagram of a cross-section of one site of an embodiment of a multi-site assay apparatus, taken along line 1.1-1.1 of FIG. 1.4, having a top plate with a single through-well, a transparent bottom plate, a mechanical or geometric hydrophobic barrier enclosing a blind cavity between the top and bottom plate, and clamping components to clamp the top and bottom plates together.

FIG. 1.2 is a schematic diagram of a cross-section of one site of another embodiment of a multi-site assay apparatus, having a top plate with a single through-well, a transparent bottom plate, a chemical hydrophobic barrier enclosing a blind cavity between the top and bottom plates, and clamping components to clamp the top and bottom plates together.

FIG. 1.3 is a schematic diagram of a cross-section of one site of another embodiment of a multi-site assay apparatus, having a top plate with a single through-well, a transparent bottom plate, a mechanical or geometric hydrophobic barrier and a chemical hydrophobic barrier which together enclose a blind cavity between the top and bottom plates, and clamping components to clamp the top and bottom plates together.

FIG. 1.4 is a schematic diagram of a top view of one site of the multi-site assay apparatus of FIG. 1.1, having a top plate with a single through-well, a transparent bottom plate, and a mechanical or geometric hydrophobic barrier enclosing a blind recessed cavity between the top and bottom plates, with a schematic representation of a concentration gradient of a chemoattractant test compound and subpopulations of cells responding within the test site, according to an embodiment.

FIG. 1.5 is a schematic diagram of an enlarged cross-sectional view of a detail of the site shown in FIG. 1.4 of the multi-site assay apparatus of FIG. 1.1, which has a top plate with a single through-well, a transparent bottom plate, and a mechanical or geometric hydrophobic barrier enclosing a blind cavity between the top and bottom plates, with a schematic representation of a concentration gradient of a chemoattractant test compound and of cells responding within the test site, according to an embodiment.

FIG. 1.6 is a schematic diagram of a further enlargement of FIG. 1.5, showing a detail of the mechanical or geometric hydrophobic barrier at the interface between the top plate and the bottom plate. Here the barrier encloses one end of the blind cavity between the two plates, along with a schematic representation of a cell, according to an embodiment.

FIG. 1.7 is an isometric semi-transparent view of the site of the multi-site assay apparatus of FIGS. 1.1 and 1.4.

FIG. 2.1 is a schematic diagram of a cross-section of one site of another embodiment of a multi-site assay apparatus, taken along line 2.1-2.1 of FIG. 2.3, having a top plate with two through-wells, a transparent bottom plate, a mechanical or geometric hydrophobic barrier, and a recessed cavity between the top and bottom plates.

FIG. 2.2 is a schematic diagram of a cross-section of one site of another embodiment of a multi-site assay apparatus, having a top plate with two through-wells, a transparent bottom plate, a chemical hydrophobic barrier, and a non-recessed cavity between the top and bottom plates.

FIG. 2.3 is a schematic diagram of a top view of the assay apparatus of FIG. 2.1, showing a schematic concentration gradient in the gel-filled cavity and cells in a well responding and moving into the cavity, according to an embodiment.

FIG. 2.4 is a schematic diagram of a top view of one site of another embodiment of the multi-site assay apparatus of FIG. 2.1, having a top plate with two through-wells and a mechanical or geometric hydrophobic barrier, and a test compound in cell culture media in one well, showing a schematic concentration gradient in the gel-filled central cavity, with cells responding within the test site, according to an embodiment.

FIG. 3.1 is a schematic diagram of a cross-section of one site of a multi-site assay apparatus, taken along line 3.1-3.1 of FIG. 3.2, having a top plate with a through-well at each end of the site, a small tapered center through-hole, a transparent bottom plate, a cavity between the top and bottom plates, and two hydrophobic barriers, one mechanical and the other chemical, according to an embodiment.

FIG. 3.2 is a schematic diagram of a top view of one site of the multi-site assay apparatus of FIG. 3.1, having a mechanical hydrophobic barrier, and illustrating a schematic concentration gradient in the gel-filled central cavity, with cells responding within the test site, according to an embodiment.

FIG. 4.1 is a schematic diagram of a top view of an embodiment of a multi-site assay apparatus, having a through-well at the left and right ends of the test site, a middle well with a tapered through-hole, a recessed cavity, and a mechanical hydrophobic barrier, with a schematic concentration gradient and with cells responding within the test site, according to an embodiment.

FIG. 4.2 is a schematic diagram of a top view of the multi-site assay apparatus of FIG. 4.1, with a schematic concentration gradient coming from a piece of tumor or other tissue in the left well, and with cells responding within the test site, according to an embodiment.

FIG. 4.3 is a schematic diagram of a cross-section of the assay apparatus of FIG. 4.4, taken along line 4.3-4.3 of FIG. 4.4, showing a first cell suspension in the left well with a test compound that inhibits migration, a second cell suspension in the right well without a test compound, and a known chemoattractant in the middle well diffusing concentrically out across the cavity between top and bottom plates, with cells from the right well migrating into cavity, and cells from the left well not migrating, according to an embodiment.

FIG. 4.4 is a schematic diagram of a top view of the assay apparatus and cells of FIG. 4.3, showing a schematic representation of a first cell suspension in the left well with a test compound that inhibits migration, a second cell suspension in the right well without a test compound, and a known chemoattractant in the middle well diffusing concentrically across the cavity between the top and bottom plates, with cells from the right well migrating into cavity, and cells from the left well not migrating, according to an embodiment.

FIG. 4.5 is a schematic diagram of a cross-section of the assay apparatus of FIG. 4.6, taken along line 4.5-4.5 of FIG. 4.6, which is a modified version of the assay apparatus of FIG. 4.1, having a through-well at each of the left and right ends of a test site, a middle well with a tapered through-hole, a relatively deep, hence enlarged, recessed cavity, and a mechanical hydrophobic barrier, with a piece of tumor or other tissue in the left well, with an enlarged (deeper) cavity between the top and bottom plates, and with cells shown before a concentration gradient of compounds from the tumor or other tissue has formed, according to an embodiment.

FIG. 4.6 is a schematic diagram of a top view of the assay apparatus of FIG. 4.5, showing a schematic representation of a piece of tumor or other tissue in the left well, which is open to an enlarged (deeper) cavity between the top and bottom plates, and showing cells in the cavity before a concentration gradient of compounds from the tumor or other tissue has formed, according to an embodiment.

FIG. 4.7 is a schematic diagram of a cross-section of the assay apparatus of FIG. 4.1, having two through-holes, a tapered middle well with a small through-hole, a recessed cavity, and a mechanical hydrophobic barrier, with a piece of tumor or other tissue in the middle well, cell monolayers in the left and right wells, and cell suspensions with cells above the cell monolayers in the left and right wells, according to an embodiment.

FIG. 4.8 is a partially transparent isometric view of the multi-site assay apparatus of FIG. 4.1, according to an embodiment.

FIG. 4.9 is a cross-sectional isometric view of the multi-site apparatus of FIG. 4.1, taken along line 4.9-4.9 of FIG. 4.8, according to an embodiment.

FIG. 6.1 is a schematic diagram of a top view of another embodiment of a multi-site assay apparatus, having multiple wells enclosing a test site.

FIG. 6.2 is a partial cross-sectional isometric view of the multi-site apparatus of FIG. 6.1, taken along line 6.2-6.2 of FIG. 6.1, according to an embodiment.

FIG. 6.3 is a partial cross-sectional isometric view of the multi-site apparatus of FIG. 6.1, taken along line 6.3-6.3 of FIG. 6.1, according to an embodiment.

DETAILED DESCRIPTION

Figure 5:
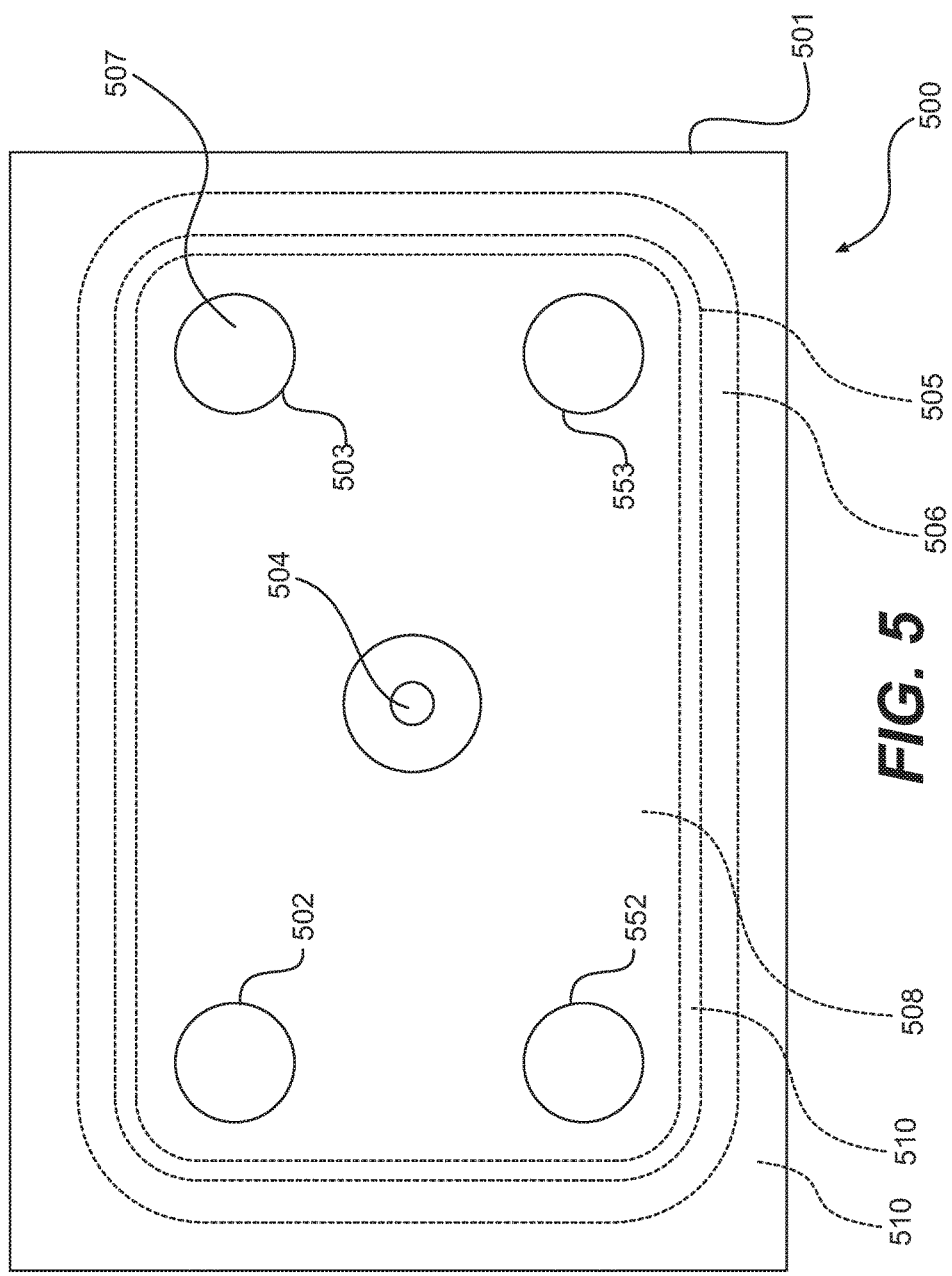
FIG. 5 is a top view schematic diagram of an embodiment of a single five-well site of a multi-site assay apparatus, having a top plate with five through-wells, a transparent bottom plate, and a mechanical or geometric hydrophobic barrier enclosing a cavity between the top and bottom plates, according to an embodiment.

Embodiments provide methods and systems for placing a test compound solution in contact with a cell suspension media containing cells, diffusing the test compound solution into the cell suspension from one or more sides, and detecting activity in the cells with respect to their distance from the side from which the test compound is diffusing.

In embodiments of side source or point source diffusion cell activity assays, a test compound may be introduced so as to initiate a stable diffusion gradient of that compound through a cell population or cell populations—to develop a diffusion gradient that is stable over a period of time. Stability in this context implies that there is no significant flow of the fluid media surrounding the cells. That lack of flow may allow detection of cell activity caused or initiated by interaction between the test compound and cells in the cell suspension according to their distance from the side source or point source from which diffusion of the test compound begins. A single image of the field of affected cells may then be captured after a specific period of time (e.g., determined in assay development) to document cell activity and the dynamics of cell activity (virtual kinetics). To accomplish this, the apparatus may prevent flow in the media that surrounds the cells for the period of time required for the diffusion gradient to be established across that field.

In one side source diffusion embodiment, the fluid of the cell suspension is constrained by both mechanical and hydrophobic barriers. The cell suspension may completely fill the site or sites of the apparatus before the introduction of the test compound solution, and consequently there may be no space into which the cell suspension can flow. In other embodiments disclosed herein, the cell suspension may not completely fill the site or sites of the apparatus, and fluid flow may be prevented by the use of a gel or gels, either in the cell suspension or next to the cell suspension. The gel may prevent the flow of fluid, but permit the establishment of a concentration gradient.

The embodiments illustrated in FIGS. 1.1-1.7, namely those with a single well or through-opening into the cavity 108, may not involve the employment of a gel in the cell suspension media, since the introduction of test compounds in aqueous solution does not cause flow of the cell suspension media in the cavity. There is nowhere for the cell suspension media to flow.

FIG. 1.1 illustrates a cross-sectional view of one site of an embodiment of a multi-site cell activity assay apparatus 100. As shown, assay apparatus 100 may include a top plate 101 (which may also be referred to as a cover) with a through-well opening 102 to the top surface 109 of a transparent bottom plate 107 (which may also be referred to as a substrate). The bottom surface 110 of top plate 101 may have a machined or otherwise formed recessed area 113. The top plate 101 may therefore have two surfaces facing the bottom plate 107: the recessed surface 113 and the remaining surface area of the bottom surface 110 of top plate 101. When the top and bottom plates are pressed together, bottom surface 110 may be in contact with top surface 109, but there may be a space—a cavity 108—between top surface 109 and recessed surface 113. Around the perimeter of cavity 108 there may be a groove 106 with a sharp corner (e.g., 90 degree corner) that creates a mechanical hydrophobic barrier 105 to fluids in cavity 108. The volume of cavity 108 may be determined by the depth of the recessed surface 113 in the bottom surface of top plate 101.

In an embodiment, the mechanical hydrophobic barrier 105 is not a pneumatic seal; thus, an aqueous solution can fill the cavity 108 between surfaces 113 and 109 by capillary action, the gas in cavity 108 being displaced by the aqueous solution and exiting through the hydrophobic seal provided by the mechanical hydrophobic barrier. When the cavity 108 is full of a fluid or gel, a test compound solution introduced into the through-well 102 may contact the fluid or gel and begin diffusing out into it from the gap between the bottom edge of through-well 102 and surface 109. That gap is the side source 112 of the concentration gradient that ensues in cavity 108. Referring to FIGS. 1.1, 1.4, and 1.7, the gap may extend substantially across the width of the test site (e.g., defined by the hydrophobic barrier), for example, within a range from over 50% of the width of the test site to 100% of the width of the test site. For example, the bottom edge of through-well 102 may span nearly the entire width of the test site, between hydrophobic barrier 105. In one embodiment, referring to FIG. 1.4, a test site may have a width of approximately 5 mm between the hydrophobic barrier 105, and a through-well 102 may have a diameter of approximately 3 mm. In another embodiment, a test site may have a width of approximately 6 mm between the hydrophobic barrier 105, and a through-well 102 may have a diameter of approximately 5 mm. In yet another embodiment, the width of the test site between the hydrophobic barrier 105 and the diameter of a through-well 102 may be substantially equal. The hydrophobic seal provided by the mechanical hydrophobic barrier 105 may ensure that cavity 108 is a "blind cavity" in the sense that through-well 102 is the only opening through which fluids can enter or exit cavity 108. The top plate 101, the hydrophobic barrier 105, and the bottom plate 107 may be held together to make and sustain contact with one another, for example, as depicted schematically in FIG. 1.1, by clamp 130 and 131. Other fasteners may be used to secure the components including, for example, threaded fasteners and adhesives.

FIG. 1.2 illustrates a cross-sectional view of one site of another embodiment of a side-source multi-site cell activity assay apparatus 103. Apparatus 103 differs from apparatus 100 of FIG. 1.1 in that the bottom surface 110 of top plate 101 has no recessed area, and the hydrophobic barrier is a chemical hydrophobic barrier 111 rather than a mechanical one. The chemical hydrophobic barrier 111 may be printed or otherwise applied to the top surface 109 of the bottom plate 107. When the top plate 101 is held in contact with bottom plate 107 (e.g., using clamp 130 and 131), a cavity 108 is formed by surfaces 109 and 110, along with the chemical hydrophobic barrier 111. The distance between surfaces 109 and 110, and therefore the volume of cavity 108, may be determined by the thickness of the hydrophobic barrier 111.

As in FIG. 1.1, in an embodiment, the hydrophobic barrier 111 is not a pneumatic seal, and an aqueous solution may fill cavity 108 by capillary action, displacing gases, which can exit through the hydrophobic barrier 111. When cavity 108 is full of a fluid or gel, a compound solution introduced into the through-well 102 may contact the fluid or gel and begin diffusing out into it from the gap between the bottom edge of through-well 102 and the surface 109. That gap is the side source 112 of the concentration gradient that ensues in cavity 108. The hydrophobic seal provided by the hydrophobic barrier 111 may ensure that cavity 108 is a blind cavity in the sense that through-well 102 is the only opening through which fluids can enter or exit cavity 108.

FIG. 1.3 illustrates a cross-sectional view of one site of another embodiment of a side-source multi-site cell activity assay apparatus 193. Apparatus 193 differs from apparatus 100 of FIG. 1.1 and apparatus 103 of FIG. 1.2 in that apparatus 193 has both a mechanical hydrophobic barrier 105 and a chemical hydrophobic barrier 111. The bottom surface 110 of top plate 101 may have no recessed area; in that case, the volume of blind cavity 108 may be determined by the thickness of the hydrophobic barrier 111.

FIG. 1.4 is a schematic diagram of a top view of one site of the side-source multi-site cell activity assay apparatus 100 of FIG. 1.1, according to an embodiment. FIG. 1.4 shows the top plate 101 with the single through-well 102, part of the top surface 109 of the bottom plate 107, and a mechanical hydrophobic barrier 105 enclosing a blind cavity 108 between the top plate 101 and the bottom plate 107. An oval groove or channel 106 formed in top plate 101 surrounds the site and, with its sharp angle (e.g., right angle) intersection with surface 110, forms a mechanical hydrophobic barrier 105 around blind cavity 108. In cavity 108 within the hydrophobic barrier 105, FIG. 1.4 shows a schematic representation (dashed lines 114 through 119) of a concentration gradient diffused across cavity 108 starting from side source 112 as represented by arrows 199, with the most concentrated part of the gradient being near side source 112 and represented by line 114, and with the least concentrated part of the gradient being farthest from side source 112 and represented by line 119.

FIG. 1.4 also shows cells (121 through 126) in a cell suspension 120 filling cavity 108, with the most responsive cells 121 located closest to the side source 112 and the least responsive cells 126 located farthest from the side source 112. Typically, the concentration gradient would be created by introducing a test compound, positive control solution, or other fluid of interest into the through-well 102 at the side source 112 and allowing the fluid to diffuse through the cell solution 120 in cavity 108.

FIG. 1.4 schematically represents a reading of the site after the concentration gradient has formed and the cells in the blind cavity 108 have responded by elongating and migrating toward the side source 112 of the concentration gradient. The shapes of the cells in these schematic representations are typical of immune cells responding to a chemoattractant. For example, the cells closest to the side source 112 of the chemoattractant react first and therefore have a higher aspect ratio (i.e., are more elongated.) However, here the cell shapes symbolically represent any morphological or other detectable (e.g., visually detectable) changes in the cell population, including internal morphological changes. By selecting representative cells at intervals across the cavity 108 and analyzing the morphology or other changes in the cells, the kinetics of the cell activity in response to the test compound may be inferred.

FIG. 1.5 illustrates an enlarged cross-sectional view of a detail of the side-source multi-site cell activity assay apparatus 100 illustrated in FIG. 1.1 and FIG. 1.4, according to an embodiment. As in FIG. 1.1, the top plate 101 may have a recessed area 113 and an oval groove 106. Apart from the groove 106, top plate 101 may have two surfaces facing bottom plate 107: the recessed area 113, which faces but does not contact the top surface 109 of the bottom plate 107, and the portion of the bottom surface 110 of top plate 101 that is not recessed or grooved and thus is in contact with surface 109 when the top and bottom plates are held together. As in FIG. 1.1, top plate 101 and bottom plate 107 may form the volume of cavity 108, the cavity 108 may be a blind cavity, and the hydrophobic barrier 105 may permit passage of gas.

Like FIG. 1.4, FIG. 1.5 shows a cell suspension 120 containing cells 121, 122, 123, 124, 125, 126. In an embodiment, the cell suspension 120 may be deposited on the top surface 109 of bottom plate 107 proximate to the side source 112 and into the cavity 108, and may fill out the cavity 108 to the hydrophobic barrier 105 and form a meniscus 127 at the opening of side source 112. A test compound, positive control, or other fluid of interest 140, placed in through-well 102, may contact the cell suspension 120 at the meniscus 127 at side source 112, and may diffuse out through the cell suspension 120, creating a concentration gradient, which is represented by lines 114, 115, 116, 117, 118, 119. The compound 140 may be most concentrated near side source 112, with lines 114, 115, 116, 117, 118, 119 representing progressively weaker concentrations of the compound 140 moving away from the side source 112. As represented in FIG. 1.5 by the differently shaped cells 121, 122, 123, 124, 125, 126, the cells 121, 122, 123, 124, 125, 126 may progressively respond to contact with the compound 140, with the strongest response at cell 121 where the concentration is highest, and the weakest response at cell 126 where the concentration is lowest.

FIG. 1.6 illustrates a further magnified schematic cross-section of a detail of the side-source multi-site cell activity assay apparatus 100 illustrated in FIG. 1.1 and FIG. 1.5, according to an embodiment. This detail illustrates an end portion of cavity 108 that is farthest from the side source 112 of the concentration gradient. As shown, the cell suspension 120 may move beyond the end of cavity 108 until the cell suspension 120 reaches the hydrophobic barrier 105, where the cell suspension 120 may form a meniscus 128 and stop moving. The fluid of the cell suspension 120 will breach the hydrophobic barrier 105 only if substantial hydrostatic pressure is applied. Since the cell suspension 120 may completely fill cavity 108 and there are no openings through which the cell suspension 120 may move, no further flow of the cell suspension 120 can occur.

FIG. 1.7 is a semitransparent isometric view of one site of the side-source multi-site assay apparatus 100 that is illustrated in FIGS. 1.1 and 1.4, according to an embodiment.

In an exemplary implementation of the embodiments illustrated in FIGS. 1.1-1.5, a single site may be part of a 48-site apparatus, in which each site may be approximately 9 mm×18 mm and the area within each site, defined by its hydrophobic barrier, may be approximately 7 mm×16 mm, with a through-well having a diameter of about 6 mm. In another embodiment, each site may be 6 mm×18 mm, and the area within each site may be oval shaped and approximately 5 mm×16 mm, with a through-well having a diameter of about 3 mm. Bottom plate 107 can be glass or a plastic material or other transparent material such as sapphire. Top plate 101 can be a plastic material, e.g., acrylic, or other suitable material.

Although figures herein illustrate a single assay or test site, one of ordinary skill in the art can appreciate that the illustrated structures could be replicated in multiple-site apparatus, for example, apparatus having 24, 32, 48, 96, 192, 364, 768, or 1536 sites.

An embodiment provides a method for performing a cell activity assay using the exemplary apparatus 100 shown in FIGS. 1.1 and 1.4-1.6. According to this method, a cell suspension 120 (containing cells suspended in a cell suspension media) may be deposited onto the top surface 109 of the bottom plate 107 and next to the side source 112 between the top surface 109 of bottom plate 107 and the recessed surface 113 of the top plate 101. The cell suspension 120 may then fill the cavity 108 between surfaces 113 and 109 and bounded by the hydrophobic barrier 105. The apparatus may then be incubated, which allows the cells 121 through 126 to adhere to the top side 109 of the bottom plate 107. The sites may then be read and recorded to provide a baseline reading of cells, or this step can be done immediately after the test solution is introduced.

The test compound solution 140 may then be deposited on the top surface 109 of bottom plate 107 next to the side source 112 between top surface 109 of bottom plate 107 and recessed surface 113 of top plate 101. The test compound solution can be deposited, for example, by pipetting, by a pin applicator, or by other appropriate means.

With test compound solution 140 deposited on the top surface 109 of the bottom plate 107, and next to side source 112, the test compound solution 140 may be in contact with cell suspension 120 at the side source 112. With this contact, test compound solution 140 may begin diffusing into the media of cell suspension 120. The site may then be read periodically to observe the effect of the test compound solution 140 on the cells 121-126 as this diffusion progresses. These readings may detect, for example, cell elongation and orientation, other morphological changes, temperature changes, movement of molecules and structures within a cell, and electromagnetic changes. Detecting morphological changes involves, for example, examining the aspect ratio (length to width ratio) of the cells. Detecting cell orientation involves, for example, examining the orientation of the aspect ratio in relation to the side source 112 from which the test compound solution is diffusing.

In the exemplary apparatus 100 shown schematically and magnified in FIGS. 1.5 and 1.6, cell suspension media 120 may fill the cavity 108, with a meniscus 127 formed around the bottom rim of through-well 102, i.e., at the side source 112. This configuration may provide an initial boundary (at meniscus 127) between the cell suspension 120 in the cavity 108 and fluid in the through-well 102. In this example, the cell suspension 120 may occupy the opening of side source 112 because the cell suspension 120 is deposited first at this opening with enough volume to just fill the cavity 108, wick by capillary action out to hydrophobic barrier 105, and form the meniscus 127 around the bottom of the through-well 102.

As the diffusion of the test compound solution 140 occurs, the test compound reaches the cells 121 nearest the opening of side source 112 first and then eventually, overtime, reaches the cells 122-125, and then cells 126 farthest away from the opening of side source 112. During assay development, apparatus 100 may be periodically read to determine whether and when the cells 121-126 are responsive to the diffusion gradient of test compound solution 140. If the cells are responsive, the effects are perceptible in stages, as the test compound solution 140 diffuses generally linearly from side source 112. In this manner, the progressive responses by cells 121-126 can yield both quantitative and kinetic data. From this data, the optimal time to acquire a single data set or image of the cell activity can be determined, and can be used subsequently to acquire a single data set or image of the test sites that captures both quantitative and kinetic information about the effects of the test compound on the cells in the cell suspension.

In the exemplary apparatus 100 shown in FIGS. 1.5 and 1.6, cell suspension media 120 may fill the cavity 108, with a larger meniscus 127 formed at the open aperture of side source 112 of cavity 108 and a smaller meniscus 128 formed at the mechanical hydrophobic barrier 105. This configuration may provide an initial boundary (at meniscus 127) between test compound solution 104 and cell suspension 120. In this example, the cell suspension 120 may occupy cavity 108 by being deposited at the side source 112, filling the cavity 108 by capillary action, and forming the meniscus 127 at the opening of side source 112.

Apparatus 100 may be periodically read as the diffusion continues and the test compound solution 140 reaches distances farther from the side source 112, as represented by the gradient lines 114-119 in FIG. 1.4. When the apparatus 100 is read at these increments of diffusion, cells within the respective gradient lines may show a response (assuming the cells are responsive to the test compound solution). Moreover, all of the cells within the outermost gradient line that the test compound solution 140 has reached may show varying degrees of response. For example, if the test compound solution 140 has reached the fourth gradient line 117, the cells 121 within the second gradient line 115 may show the most response and the cells 123 between the third gradient line 116 and the fourth gradient line 117 may show the least response, with the cells 122 between the second gradient line 115 and the third gradient line 116 showing a response somewhere in between.

Each of FIGS. 2.1-2.4, 3.1-3.2, and 4.1-4.9 illustrates one site of a multi-site cell activity assay apparatus (200, 300, and 400 respectively), according to other embodiments. Apparatus 200, 300, and 400 are similar in most respects to the apparatus 100 illustrated in FIGS. 1.1-1.7, except that apparatus 200, 300, and 400 have a second through-well or opening in the top plate. As shown in FIGS. 2.1-2.4, apparatus 200 includes through-wells 202 and 203 in top plate 201. As shown in FIGS. 3.1-3.2, apparatus 300 includes through-wells 302 and 303 in top plate 301, as well as a center small through-hole 304 through top plate 301. As shown in FIGS. 4.1-4.9, apparatus 400 includes through-wells 402 and 403, as well as a center well with a small through-hole 404 in the bottom that goes through top plate 401. These embodiments and the related variations are topologically different from apparatus 100 in that the cavities 208, 308, and 408 formed between the top surfaces 209, 309, and 409 of the bottom plates 207, 307, and 407 and the bottom surfaces 210, 310, and 410 (or the recessed portions 213, 313, and 413 of the bottom surfaces) of the top plates 201, 301, and 401 are not "blind" cavities; i.e., there are multiple ways for fluids to enter and exit these cavities.

FIGS. 2.1, 2.3, and 2.4 represent one site of apparatus 200, a multi-site side-source cell activity assay apparatus according to an embodiment. Sites of apparatus 200 may each have two through-well openings 202 and 203 in the top plate 201. Through these wells, fluids (e.g., cell suspensions, media, test compounds, positive control solutions, and other fluids of interest) may be introduced. A cavity 208 may be provided between the top surface 209 of the transparent bottom plate 207 and, in FIG. 2.1, the recessed portion 213 of the bottom surface 210 of the top plate 201. Alternatively, as shown in the alternate cell activity assay apparatus 250 in FIG. 2.2, the bottom surface 210 of top plate 201 may have no recessed area, so cavity 208 is formed between surfaces 209 and 210. Cavity 208 may be bounded at its perimeter by a hydrophobic barrier, either mechanical 205 (e.g., a structural corner of a groove or channel 206), as in FIG. 2.1, or chemical 211, or both, as in FIG. 2.2. The volume of cavity 208 may be determined by the distance between surfaces 213 and 209 in FIG. 2.1, and between surfaces 210 and 209 in FIG. 2.2. A hydrophobic barrier around a site may not be a pneumatic seal, so that gasses may escape from the cavity through the hydrophobic barrier. Cavity 208 is not a "blind" cavity, since there are two openings—through-wells 202 and 203—through which fluids may enter and exit.

In FIGS. 2.1 and 2.2, a suitable quantity of a fluid, e.g., a liquid cell suspension, may be placed in the bottom of a through-well, such as through-well 202, at the side source 212, which may be the gap between surface 209 and the edge of the through-well 202 closest to the rest of the site. As shown in FIG. 2.3, the gap may extend substantially across the width of the test site, for example, extending across nearly the entire width between hydrophobic barrier 205. In embodiments, the gap may extend substantially across the width of the test site (e.g., defined by the hydrophobic barrier), for example, within a range from over 50% of the width of the test site to 100% of the width of the test site, as described above in reference to FIGS. 1.1, 1.4, and 1.7. The fluid suspension may move out from the side source 212 by capillary action into the cavity 208, filling the cavity 208 by spreading between surfaces 209 and 213 (FIG. 2.1), or 209 and 210 (FIG. 2.2), as far as the hydrophobic barrier 205 (FIG. 2.1) or 211 (FIG. 2.2) surrounding the site. The fluid of the cell-suspension media may breach hydrophobic barrier 205 or 211 only if substantial hydrostatic pressure is applied, but, because of surface tension, the fluid may not move into the portions of surface 209 that form the bottoms of the through-wells 202 and 203. The gap at the bottom edge of the well closest to the rest of the site—between surfaces 213 and 209 in FIG. 2.1, or between surfaces 210 and 209 in FIG. 2.2—may provide a side source 212 from which a fluid can move by capillary action to fill the cavity 208, or to diffuse across the cavity 208 through a liquid or gel, forming a concentration gradient.

FIGS. 2.1-2.4 illustrate methods of employing apparatus 200. In an embodiment, a method may first introduce into the cell suspension media a gelling compound in liquid phase that is temperature sensitive, pH sensitive, or sensitive to another change in conditions. The liquid cell suspension media with gelling compound may then be introduced into either through-well 202 or 203 at the side source 212, and may fill the cavity 208, as described above. Since cavity 208 is not a blind cavity, as long as the cell suspension is in a liquid state, the cell suspension may flow within the cavity 208. After the media or cell suspension has filled cavity 208, flow may be prevented by allowing or inducing the media to become a gel, e.g., by implementing appropriate changes in conditions that induce the media to gel.

In FIG. 2.3, which illustrates a top view of one site of the apparatus 200 of FIG. 2.1, the initial introduction of cell suspension media 220 contains no cells. The cell suspension media 220 moves into cavity 208 by capillary action and fills the cavity 208 out to the hydrophobic barrier 205 except for the portions of the surface 209 that form the bottoms of through-wells 202 and 203. The cell suspension media 220 may then be induced to gel. A test compound 240 may be introduced into through-well 202, may contact the gelled cell suspension media 220 at side source 212, and may diffuse across cavity 208 starting from side source 212 as represented by arrows 299, forming a concentration gradient represented by dashed lines 215, 216, 217, and 218. Line 215 represents the most concentrated level of test compound 240, while line 218 represents the least concentrated level of test compound 240. Cell suspension containing cells may be introduced into through-well 203. When the diffusing test compound 240 reaches through-well 203, the cells begin to respond. For example, as shown in FIG. 2.3, the cells 221, 222, and 223 may elongate, orient, and migrate toward more concentrated levels of test compound 240. As shown, cells 221, 222, and 223 may exhibit increasing responses to increasing concentrations of test compound 240 as the cells 221, 222, and 223 migrate across cavity 208. Data may be recorded at any point or points during this process for use in assay development, or as a reading during an assay.

FIG. 2.4 is another top view of one site of multi-site apparatus 200. Here, the site is prepared by introducing a cell suspension 220 (e.g., including media and cells) at a side source 212 (e.g., the opening, or gap, at the bottom edge of one of the through-wells 202 and 203, which may extend substantially across the width of the test site). The cell suspension 220 fills cavity 208 out to hydrophobic barrier 205, not flowing into the portions of surface 209 that form the bottoms of through-wells 202 and 203. The cell suspension 220 may be induced to gel, preventing any further flow within the cell suspension 220. Cell suspension media without cells or gelling-compound may be introduced into wells 202 and 203, the apparatus may be incubated for an optimal period (determined during assay development), after which a test compound 240 may be introduced into well 203 (after removing any media). The test compound 240 diffuses starting from side source 212 as represented by arrows 299, and through the gelled cell suspension 220 and across cavity 208, forming a concentration gradient, which is represented in FIG. 2.4 by the series of dashed lines 219, 218, 217, 216, and 215. The concentration is greatest at line 219, and weakest at line 215. As the test compound 240 diffuses, the cells in the cavity may begin to respond to the test compound 240, as represented by the different shapes and elongations of cells 221, 222, 223, 224, and 225. Cells 221 are contacted first by the test compound 240, are exposed longest, and experience the most concentrated level of test compound 240. Cells 224 respond to the weakest concentration of test compound 240, and for the least amount of time. The test compound 240 has not reached cells at 225; thus, those cells are not responding. Here again data can be recorded at any point or points in time during this process for use in assay development, or as a reading during an assay.

FIGS. 3.1-3.2 and FIGS. 4.1-4.4 illustrate other embodiments of side-source diffusion, including cell activity assay apparatus 300 and 400, respectively. In those embodiments, two wells or openings 302, 303 and 402, 403 may be provided through the top plate 301, 401, through which cell suspension media and test solutions may be introduced, as well as a third through-hole 304, 404 between the other two wells or openings. The process to set up an assay with these embodiments is similar to that described above in reference to FIG. 2.4 for the cell activity assay apparatus 200, but differs after the cell suspension fluid has gelled (by, for example, temperature change, PH change, or other changes in condition). Test solutions, media solutions, cell suspensions, pieces of tissue, and sintered material containing test compounds are some of the substances that can, without causing the cell suspension to flow, be introduced using the three through-holes. If point source diffusion is desired, the test solution may be introduced through the center well through-hole 304, 404, such that the diffusion gradient forms concentrically from that through-hole. If the test solution is introduced from either of the side wells 302, 303 or 402, 403, the diffusion gradient develops from that side well, which is referred to herein as a "side source" of compound diffusion. Note that the two- and three-well configurations 200, 300, 400 that use gel to prevent flow of the cell suspension not only enable cell activity assays of a simple one-compound one-cell type, but may also be used for numerous more complex assays employing multiple cell types and multiple compounds.

As with the cell activity assay apparatus 100 and 200, the cell activity assay apparatus 300 and 400 demonstrate ways in which the present embodiments are able to provide not only quantitative data (e.g., number or percentage of cells affected) but also kinetic data (e.g., patterned response of the cells over time) and dose-response data (as the amount of test compound contacting cells decreases with distance from the point of origin of diffusion). By observing patterns of cell responses occurring at different distances from the source, the present embodiments also remove doubt as to whether an actual response (or "hit," in the language of High Content Screening and High Throughput Screening assays) is detected, because the responses can be detected progressively in accordance with their distance from, and thus their time of first contact with, the source of the test compound. Thus, the present embodiments may achieve coefficients of variation significantly lower than those of the prior art.

Referring again to FIGS. 3.1-3.2 and FIGS. 4.1-4.4, the small, tapered central through-holes 304, 404 of cell activity assay apparatus 300, 400 enable a variation on the above-described methods of introducing fluids into sites of the apparatus. If the central tapered through-hole 304, 404 is used to introduce the cell suspension media (with or without cells), and if a pipette is employed for this purpose with a tip-end diameter larger than the bottom diameter of tapered through-hole 304, 404, and the pipette tip is pushed into the tapered through-hole 304, 404 until a hydraulic seal is created, then the expression of the cell suspension introduces the cell suspension media into the cavity 308, 408 by hydraulic force. In some assays, this may be advantageous since the cavity 308, 408 is force-filled from the center and cells in the cell suspension are distributed uniformly within the cavity 308, 408. If the volume of the expressed cell suspension is slightly larger than the volume of the cavity 308, 408, the volume of the expressed cell suspension will provide enough fluid to fill the site out to the hydrophobic barrier 305, 311, 405, 411, (whether that barrier is mechanical, chemical, or both) including the portions of surface 309, 409 that form the bottoms of through-wells 302, 303, 402, 403. Alternatively, the volume of the cell suspension media introduced in this way can be larger than the minimum volume required to fill the cavity 308, 408, and the thin space out to the hydrophobic barrier 305, 405, in which case the cell suspension media may partially fill the wells 302, 303, 402, 403. After the cell suspension media has gelled, test compound solution (or tissue 442 as in FIG. 4.2) that is introduced into a through-well 302, 303, 402, 403 will be farther from the opening, or gap, of the side source 312, 412 into the cavity 308, 408 into which it will eventually diffuse and set up a concentration gradient (as represented by dashed lines 316, 317, 318, 319 (FIGS. 3.2) and 416, 417, 418, 419 (FIGS. 4.1 and 4.2)) across the field of cells (as represented by cells 321, 322, 323, 324, 325 (FIGS. 3.2) and 421, 422, 423, 424, 425 (FIGS. 4.1 and 4.2)) in the cavity 308, 408. This will cause a delay in the development of the diffusion gradient in cavity 308, 408, which may be advantageous for some assays. Alternatively, media with liquid-phase gel, but without cells, may be added to the wells and/or through-hole (302, 303, 304; 402, 403, 404; or some combination thereof) after the initial introduction of the liquid phase of the cell suspension and its subsequent gelling. The volume (amount) of this second liquid-phase media introduction may determine how high it fills the well and/or through-hole (302, 303, 304; 402, 403, 404; or a combination thereof), and consequently how long the delay before the test compound concentration gradient forms in the cavity 308, 408.

The embodiments illustrated in FIGS. 3.1-3.2 and FIGS. 4.1-4.4 may also be used for more complex assays involving several different compound solutions, one diffusing from well 302, 402, another from well 303, 403, and a third from the small center through-hole 304, 404. These methods may also be used to ascertain whether and to what extent a test compound can inhibit a certain cell activity. For example, a known chemoattractant can be introduced through the small center through-hole 304, 404 (or to a side well 302, 303; 402, 403), and compounds to be tested for their ability to inhibit chemotaxis or other cell activity may be introduced to the other wells. The resulting interactions may then be compared to a second site in which media with no test compound (or fewer test compounds) is used.

As described above, the present embodiments may allow the determination of cell activity by detecting changes in cells that are indicative of a response to a test compound solution and that occur well before a cell could migrate through a membrane. These changes include, for example, cell orientation, internal morphological changes, temperature variations, molecular movement within the cell, and electromagnetic changes. The most appropriate method of detecting these changes depends upon the types of compounds and cells that are under investigation. With any of these methods, the present embodiments may provide the ability to unambiguously detect the kinetics of cell change, based on the fact that the test compound concentration gradients, and the cells' activity, advance or progress linearly or concentrically from an opening into the cell suspension.

As one example of detecting cell changes, an infrared reader could be used to monitor changes in the temperatures of cells. The cells could be immune cells, for example, that are exposed to compounds in the test compound solution that trigger a metabolic response in the immune cells. This metabolic reaction raises the temperature of the cells. Repeated scans by the infrared reader detect this rise in temperature. In addition, when side and point diffusion sources are used, the infrared reader can observe the effects caused by the concentration gradient, as cells closer to the test compound solution diffusion source respond first. The rise in temperature could continue as well, creating a temperature gradient among the cells, which could be another source of kinetic data.

As another example of detecting cell changes, a light reader, detector, or image-acquisition instrument could be used to monitor movement within fluorescent-labeled cells. The cells could, for example, be tagged with green fluorescent protein. In this manner, well before a cell could orient itself, change in shape, or move toward the source of the test compound solution, the reader could document movement internal to the cell.

As another example of detecting cell changes, a microscopic detection system could be used to detect changes in cell shape and orientation. As a precursor to moving, cells typically undergo morphological changes (e.g., changing their aspect ratio) and orient toward the diffusion source of a test compound solution. Thus, these changes can be observed well before the cell migrates. Examples of suitable microscopic detection systems are the confocal microscopy detection and imaging systems produced by Atto Bioscience of Rockville, Md.

In another alternative embodiment of the cell activity assay apparatus 300 and 400, the test compound solution may be contained in a sintered material that holds the test compound solution and releases it slowly in a controlled manner.

In the embodiment illustrated in FIGS. 4.3 and 4.4, the site may be prepared by filling cavity 408 with a gelling suspension media containing no cells, which may then be allowed to gel. Then, cell suspension 420 containing cells may be introduced into through-wells 402 and 403, providing a boundary 412 at which the cell suspension 420 is in contact with the gelled suspension media in the cavity 408. The cells 433 in through-well 402 may then be treated with a test compound that may inhibit cell response. A known chemoattractant 427 may be introduced into center through-hole 404 and allowed to diffuse concentrically from center through-hole 404 through cavity 408, forming the concentration gradient represented by lines 435-441 in FIGS. 4.3 and 4.4. The concentration would be high at 435, low at 441. The cells in well 403, which have not been treated with the response-inhibiting test compound, respond to the test compound (413-415 in FIG. 4.4), elongating and migrating toward increasingly concentrated levels of the chemoattractant 427, as shown in FIGS. 4.3 and 4.4. Cells 433 in well 402 have been treated with the response-inhibiting test compound, and are therefore not responding to the chemoattractant 427, demonstrating that the test compound is an effective inhibiter.

FIGS. 4.5 and 4.6 are schematic diagrams of one site of a modified version of the assay apparatus of FIG. 4.1, according to an embodiment. In the modified version shown in FIGS. 4.5 and 4.6, the apparatus is similar to that shown in FIGS. 4.3 and 4.4, except that the recessed area 413 in the bottom of top plate 401 is deeper than that shown in FIG. 4.3, which results in a larger volume cavity 408 with a greater depth between surfaces 413 and 409. The recessed portion 413 of the top plate may be confined to an oval-shaped area that may intersect with the bottom edges of wells 402 and 403 over a limited segment rather than encircling the wells completely, as in FIG. 4.4. Then, the un-recessed area 410 of the top plate may have the shape of an oval defined by hydrophobic barrier 405. This oval 405 encloses another oval (area 413) with a circle at each end (through-wells 402 and 403).

FIGS. 4.5 and 4.6 show cells 475 in the cavity 408 and a piece of tumor or other tissue 460, in media, in well 402. As yet no concentration gradient of compounds emanating from the tissue has formed across the cavity. A cell suspension with cells 475 may have been introduced into the cavity 408 in ungelled form through tapered through-hole 404, using a volume of said suspension just sufficient to fill cavity 408, excluding the parts of surface 409 that form the bottoms of wells 402 and 403, after which the cell suspension may have been allowed or induced to gel. With the site thus prepared, a piece of tumor or other tissue 460 in media 488 may be introduced into well 402 (or 403, since the wells are symmetrical). Media 488 may be cell-culture media in liquid form. Other cell-culture media 477 and 478 may be introduced into well 403 and the top portion of the well of through-hole 404 to sustain the cells in assays with long incubation times. The apparatus may be incubated and then read with an appropriate detection system. Digital image HCS detection instruments with image-analysis software may be optimal for this purpose. The cells 475 may, for example, be killer T-cells that have received a treatment, being tested, that may sensitize them to compounds emanating from the tissue so that the cells 475 move toward the tissue. The cells may not respond to compounds diffusing from the tissue sample (indicating that the treatment has not been efficacious), or they may respond by approaching the tissue (indicating that the treatment has been effective). Since the deeper cavity 408 may permit a relatively thick multilayer of cells 475, this embodiment may be used in studies that must have such a multilayer, for example, longer-term studies of angiogenesis—of the power of tumor tissue to induce angiogenesis and the ability of test compounds to impede or reverse angiogenesis, among others.

FIG. 4.7 is a schematic diagram of a cross-section of one site of the assay apparatus of FIG. 4.1, having two through-wells 402 and 403, a middle well with a small tapered through-hole 404, a recessed cavity 408, and a mechanical hydrophobic barrier 405. A piece of tumor or other tissue 430 is shown in the middle well, cell monolayers 433 and 434 are schematically depicted in wells 402 and 403, and cell suspensions 428 and 429 are shown above the cell monolayers in wells 402 and 403, according to an embodiment. In one method for using the apparatus depicted in FIG. 4.7, ungelled cell culture media without cells 426 may be introduced into the apparatus through the center well with through-hole 404 in sufficient volume to fill the cavity 408 and partially fill the wells 402 and 403. The media 426 may be allowed or induced to gel, and then cell suspensions with cells may be added to wells 402 and 403 to form the cell monolayers 433 and 434. The apparatus may then be incubated until cell monolayers 433 and 434 form. Subsequently, cell suspensions 428 and 429 with cell populations 431 and 432 may be introduced into wells 402 and 403, and a tissue sample 430 in media 427 is introduced into the center well, with through-hole 404. The apparatus may then be incubated and then read with a HCS instrument, once or many times, as appropriate, to determine whether and to what extent the cells in population 431 and 432 (which may be the same or different) respond to the compounds diffusing from the tissue 430 and penetrating the cell monolayers 433 and 434. Digital image HCS detection instruments with image-analysis software are optimal for this purpose. Researchers practiced at the art will appreciate that many other assays may be performed with this embodiment.

FIGS. 4.8 and 4.9 are semi-transparent isometric views of one site of the side-source multi-site assay apparatus 400 of FIGS. 4.1-4.4 and 4.7. FIG. 4.8 is a schematic ¾ view of a single site, and FIG. 4.9 is a cross-sectional view taken along line 4.9 of FIG. 4.8.

FIG. 5 is a top-view schematic diagram of an embodiment of a single five-well site of a multi-site assay apparatus 500 having a top plate 501 with four through-wells 502, 552, 503, and 553, one in each corner, a central well with a small tapered through-hole 504, a transparent bottom plate 507, and a mechanical or geometric hydrophobic barrier 505 enclosing a cavity 508 between the top and bottom plates according to an embodiment. The assay method is similar to above described embodiments except that more options are provided for more elaborate assays, for example, ones involving four different cell populations deposited into the four corner wells, and tumor or other tissue in the central well. Alternatively, ungelled cell suspension may be deposited in the cavity 508 through the through-hole 504 of the central well, and allowed to gel. Various test compounds and or inhibitors then may be deposited in the corner wells.

FIGS. 6.1-6.3 illustrate top and partial cross-sectional views of an embodiment of an assay apparatus having eight sites, each of which is a multi-well site having a top plate 601 with eighteen peripheral through-wells 661-669 and 671-679, two end wells 660 and 670, a tapered central through-hole 604, a transparent bottom plate 607, a mechanical or geometric hydrophobic barrier 605 enclosing the site, and a cavity 608 between the top and bottom plates, according to an embodiment. This embodiment may be used for long-term cell activity assays in which cells may be cultured in the central cavity 608 between the top plate 601 and the transparent bottom plate 607 of each of the eight sites. In each site, ungelled cell suspension may be introduced through the central tapered through-hole 604 and then allowed or induced to gel. The twenty peripheral through-wells 660-679 may then be filled with standard (non-gelling) cell culture media (which can be replaced periodically with fresh media to promote cell growth, cell differentiation, cell proliferation, and tissue development), and the apparatus may be incubated. Periodic or continuous readings of the cell cultures in the eight sites using a HCS instrument or an inverted microscope, may then be done. When the cell cultures develop to the desired state (for example, angiogenesis, development of other kinds of tissue, or differentiation of stem cells), test compounds may be introduced through one or more of the twenty peripheral through-wells to assess their effect on the cell cultures. Alternatively, one or more cell suspensions may be introduced through one or more of the peripheral through-wells and the interaction may be monitored between these new cells and the cell cultures already in the apparatus. The depth of the cavities (the distance between the top surface 680 of the bottom plate 607 and the bottom surface 681 of the recessed areas of the top plate 601) can be adjusted to suit the intended assay; if development of thick tissue is desired, the recessed areas in the top plate 601 may be made deeper. Although for descriptive purposes the embodiment of FIGS. 6.1-6.3 includes a particular number of sites, a particular number of through-wells at each site, and a particular layout of the sites and through-wells, other embodiments could use different numbers of sites and through-wells and different layouts, as appropriate for particular implementations and for desired manufacturing methods.

Although, for clarity, the figures do not show a lid on a cell activity assay apparatus, any of the embodiments described herein could include a lid over the apparatus (e.g., over the top plate 101 of FIG. 1.1). A lid may help minimize evaporation and protect the contents of an apparatus during transport.

Although embodiments described above illustrate circular through-wells that are generally more susceptible to manufacturing (e.g., by drilling or molding), such as through-well 102 in FIG. 1.4, other embodiments may use differently shaped through-wells. For example, through-wells may be square, rectangular, or triangular, which may provide a true linear side aperture (when viewed from a plan view as in FIG. 1.4) from which to diffuse a test compound. Accordingly, notwithstanding the benefits associated with a circular through-well, the present embodiments should be considered broadly applicable to any shaped through-well that provides a desired side-source diffusion.

Although embodiments described above involve cell suspensions that may be incubated to allow cells to settle and adhere to the top surface of a bottom plate (e.g., top surface 109 of bottom plate 107 of apparatus 100 of FIG. 1.1), alternative embodiments may accommodate assays with cells that do not adhere to a surface and instead stay suspended in the cell suspension media or gelled cell suspension media. These non-adherent cells could include, for example, sperm or bacteria. In these cases, the effect of the diffusion gradient may still be observed. In other words, even if the cells are moving, a researcher may observe the progressive effect as the test compound solution diffuses farther from the side source or point source, and reaches and activates additional cells. Where a gel in liquid phase is employed in the cell suspension, and where the cell suspension is allowed to gel as in embodiments of the cell activity assay apparatus 200, 300, and 400, the use of non-adherent cell types may be facilitated.

According to other embodiments, a test compound from a compound library may be applied in liquid form to a particle or bead. The liquid test compound may then be gelled or dried on the particle or bead or allowed to be absorbed into the particle or bead. The particle or bead may then be submersed in a cell suspension media having cells (either settled and adhered to a surface, or non-adherent), after which diffusion from the particle into the cell suspension media may occur and the effect on the cells may periodically read. The particle or bead may be coded (e.g., color coded beads having bands of color) to indicate what testing compound solution has been applied. The particles or beads may be coated with media-soluble coating (e.g., water-soluble). The particles or beads may be small vessels, e.g., pieces of capillary tubing or hollow balls having a small hole in their surface. In the case of hollow balls, the balls may be filled by applying a vacuum while the balls are in a test compound solution. When the vacuum is released, the solution may fill the balls. The particles or beads may also be porous sintered material, e.g., metal, plastic material, glass, or ceramic particles coded by color, shape, or some combination thereof. These particles may be filled with test compound solution using a vacuum in a manner similar to the hollow balls.

The present embodiments are adaptable to a variety of assay formats. As one example, present embodiments may be applied to assay apparatus complying with the Society for Biomolecular Screening (SBS) Microplate Format. Such apparatus may employ individual microplates having 8, 16, 32, 48, 96, 192, 384, 768, or 1536 sites, which are typically used in automated systems that assay a high number of compounds. The various embodiments of the individual site constructions described above may be replicated across the multiple sites of the SBS plate. However, the use of these individual site constructions is not limited to the SBS format, and may indeed be applied to other standard and non-standard formats.

The present embodiments may provide many surprising benefits, including but not limited to one or more of the following:

1) use few cells;
2) use small amounts of test compound;
3) complete assays up to 10-1000 times faster than conventional live-cell based assays;
4) lower costs by enabling high density studies (i.e., low cost per test per compound);
5) lower coefficients of variation, for example, preventing coefficients of variation due to pipetting errors from passing through to the coefficients of variation of the assay, which may enable cell based HCS and HTS;
6) obtain kinetic data as well as quantitative data, in contrast to, for example, migration assays that count the number or percentage of cells that have passed through a filter, but yield no data about the cells that have not passed through the filter;
7) reduce reagent costs by virtue of the low number of cells and low volume of compounds needed;
8) provide optically advantageous assay apparatus that enable relatively distortion-free viewing by high-resolution optical detection systems;
9) enable the use of primary cells, e.g., cells directly from patients, as opposed to immortal cell lines;
10) provide apparatus that are geometrically compatible with high resolution optical detection systems, which require flat, transparent, relatively thin bottom plates (between 0.1-2.0 mm thick); and
11) help avoid evaporation problems by confining the cell suspension and test compounds in an easily-sealed environment.

The benefits of the present embodiments are even more apparent when considering differences from conventional approaches, such as Zigmond chambers. First, adherent cells and only adherent cells are used in a conventional Zigmond chamber. Second, the process of the assay is different. With a conventional Zigmond chamber, the cells are first placed on a bottom surface of a top plate (e.g., a cover glass), allowed to adhere to the bottom surface, and then the cells and fluid that are not in a strip down the middle of the bottom surface of the top plate are completely removed so the top plate is dry except in that middle strip. The top plate is then inverted onto the middle of the bottom plate (e.g., a 2 mm thick microscope slide with two grooves ground in it 4 mm wide and 1 mm deep, with a 1 mm wide ridge in between). The cells and accompanying media are held between the top plate (e.g., a cover glass) and the top of the ridge of the bottom plate. The top and bottom plate are then clamped together. Then media is wicked into one bottom-plate groove and media with test compound is wicked into the other. The apparatus is then incubated again for a period long enough for the cells to respond. The cells that have responded (e.g., elongated in the direction of the test compound groove) are counted along with the cells that have not responded. If a significant proportion of the total cell population has responded, it is inferred that the test compound is a chemotactic factor.

The present embodiments (e.g., cell activity assay apparatus 200, 300, 400, 500) are distinguishable from conventional approaches, such as Zigmond chambers, in many other respects, including but not limited to:

(1) the present embodiments may provide multi-site apparatus;

(2) the present embodiments may enclose cell suspension and test compound solutions between plates that can be covered or enclosed to prevent or restrict evaporation;

(3) the present embodiments may provide ample volumetric capacity to allow the option of sustaining long term tissue cultures;

(4) in the present embodiments, the volumes of tissue culture media may be repeatedly renewed without disturbing the cells in the apparatus;

(5) the present embodiments may permit a host of complex assays involving multiple cell types and multiple compounds (see, e.g., cell activity assay apparatus 200, 300, 400, and 500);

(6) the present embodiments may allow for assays that involve point source diffusion, side source diffusion, and both together (see, e.g., cell activity assay apparatus 300, 400, and 500);

(7) the present embodiments may allow the use of pieces of tissue as sources of compounds to effect change in the cells of an assay (see, e.g., cell activity assay apparatus 200, 300, 400, and 500);

(8) the present embodiments may be constructed to alter the space between plates and therefore volume of the cell suspension, whether gelled or otherwise;

(9) the present embodiments may be completely assembled prior to the introduction of the cell suspension(s);

(10) in configurations as SBS-compatible multi-site assay platforms, the present embodiments may enable automated data collection and analysis in high content screening platforms (instruments), and the repeated collection of data from sites of interest, if any;

(11) the present embodiments may enable the use of non-adherent cells and adherent cells in the same assay; and

(12) the present embodiments may enable the long term culture of cells so that the cells may form interconnected tissue, for example, capillary tissue formed from endothelial cells, which tissue may then be studied for interaction with other types of cells and compounds or other tissue of interest (see, e.g., cell activity assay apparatus 400 and 500).

Overall, the present embodiments may allow researchers to gather cell data related to, for example, cell orientation, shape, morphology, and intra cellular movements of molecules. In complicated assays such as those involving angiogenesis, the present embodiments may facilitate the collection of data on whether angiogenesis is observed. In addition, more data may then be gathered by, for example, adding different compounds to the cells undergoing angiogenesis to determine if the angiogenesis can be reversed or inhibited.

Obtaining kinetic data may also significantly lower the coefficient of variation of a study. With traditional cell activity assays, large variations in test sites as well as positive and negative control sites can result in unacceptably high coefficients of variation. Indeed, researchers usually use duplicate or triplicate sites for each test compound and repeat traditional cell activity assays two and three times to confirm results. In contrast, the present embodiments may facilitate kinetic studies that significantly lower the coefficient of variation.

These kinetic studies may identify changes in the cells and cell populations progressively. A researcher (or detection system) may observe a pattern as cell activity progresses geometrically through a population of cells as a test compound diffuses through that population, or observe no progressive pattern. Changes in cell activity progressing geometrically (in a linear or concentric pattern) in lock step with the diffusion of a test compound in that same pattern may be qualitatively different from assays that cannot use kinetic patterns. Detecting these patterns may establish a causal relationship. Therefore, the present embodiments may virtually eliminate false positives and the irregularities common with current cell based assays.

A researcher using the present embodiments may also determine when cells that are responsive to the test compound solution are affecting adjacent cells. For example, by monitoring the diffusion rate of the test compound solution, a researcher may determine when cells should respond, based on their distance from the side source or point source. If such cells show changes before that time, then the researcher may deduce that they are being affected by adjacent cells before the test compound solution reaches them. Such information could be especially valuable for secondary and tertiary screens.

Although the present description and figures may refer to a single side source or a single point source, embodiments may include multiple side sources or point sources in a site of a cell activity assay apparatus. What is relevant with respect to the number of the diffusion sources is that they are far enough apart for the kinetics of the phenomena being studied to be clear. For example, if there is a pattern of diffusion sources in an assay site, they are preferably far enough apart not to interfere with one another during the course of the assay. Furthermore, several diffusion sources may be used, one with a known inhibitor of a cellular activity and another with a compound from a compound library. As the diffusion front of the inhibitor intersects with the test compound diffusion front, the pattern of cell activity may show a characteristic pattern.

The foregoing disclosure of the preferred embodiments has been presented for purposes of illustration and description. It is not intended to be exhaustive or to limit the embodiments to the precise forms disclosed. Many variations and modifications of the embodiments described herein will be apparent to one of ordinary skill in the art in light of the above disclosure.

While various embodiments have been described, the description is intended to be exemplary, rather than limiting and it will be apparent to those of ordinary skill in the art that many more embodiments and implementations are possible that are within the scope of the embodiments. Any feature of any embodiment may be used in combination with or substituted for any other feature or element in any other embodiment unless specifically restricted. Accordingly, the embodiments are not to be restricted except in light of the attached claims and their equivalents. Also, various modifications and changes may be made within the scope of the attached claims.

Further, in describing representative embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the present embodiments.

What is claimed is:

1. An apparatus for exposing cells to a test compound solution to determine whether the test compound solution induces progressive cell activity response in the cells, the apparatus comprising:
    a substrate having an inner surface and an outer surface opposite to the inner surface;
    a plate disposed over the substrate such that a cavity is defined between the plate and the substrate,
        wherein the plate has a first surface and a second surface opposite to the first surface, the second surface facing the inner surface of the substrate,
        wherein the plate defines a through-well extending from the first surface of the plate to the second surface of the plate,
        wherein the through-well exposes the inner surface of the substrate, and
        wherein the through-well is in fluid communication with the cavity; and
    a hydrophobic barrier on the substrate and/or the plate,
        wherein the hydrophobic barrier defines a test site enclosing the through-well when the apparatus is viewed from a plan view perpendicular to a plane defined by the plate,
        wherein the hydrophobic barrier allows passage of gas outside of the test site while limiting passage of liquid outside of the test site,
        wherein the substrate, the plate, and the hydrophobic barrier are configured to contain the cells within the test site,
        wherein the through-well is disposed at a first side portion of the test site when viewed from the plan view, the test site having a second side portion opposite to the first side portion,
        wherein, when viewed from the plan view, the test site has a length from the first side portion to the second side portion, and the length is greater than a width of the test site,
        wherein the plate and the substrate define a gap between the substrate and an edge of the through-well at the second surface of the plate, on a side of the through-well facing the second side portion of the test site, and
        wherein the gap extends substantially across the width of the test site.

2. The apparatus of claim 1, wherein the hydrophobic barrier comprises a groove in the second surface of the plate and/or the inner surface of the substrate.

3. The apparatus of claim 1, wherein the hydrophobic barrier comprises a chemical hydrophobic barrier applied to the inner surface of the substrate and/or the second surface of the plate.

4. The apparatus of claim 1, wherein the gap extends across at least ⅗ of the width of the test site.

5. The apparatus of claim 1, wherein the test site is oval-shaped.

6. The apparatus of claim 1, wherein the through-well is circular when viewed from the plan view.

7. The apparatus of claim 1, wherein the plate defines a second through-well extending from the first surface of the plate to the second surface of the plate,
    wherein the second through-well is disposed at the second side portion of the test site,
    wherein the second through-well exposes the inner surface of the substrate,
    wherein the second through-well is in fluid communication with the cavity,
    wherein the plate and the substrate define a second gap between the substrate and an edge of the second through-well at the second surface of the plate, on a side of the second through-well facing the first side portion of the test site, and
    wherein the second gap extends substantially across the width of the test site.

8. The apparatus of claim 7, wherein the plate defines a through-hole extending from the first surface of the plate to the second surface of the plate,
    wherein the through-hole is disposed at a middle portion of the test site between the first side portion and the second side portion of the test site, and
    wherein at the second surface of the plate, the through-hole is substantially smaller in width than the through-well at the first side portion of the test site and the second through-well at the second side portion of the test site.

9. The apparatus of claim 8, wherein the through-hole comprises a tapered through-hole having a wider dimension at the first surface of the plate and a smaller dimension at the second surface of the plate.

10. The apparatus of claim 1, wherein between the gap and the second side portion of the test site, the bottom surface of the plate has a recessed portion bounding the cavity.

11. The apparatus of claim 1, wherein the substrate is transparent and has a thickness from the inner surface to the outer surface within a range of about 0.1 mm to 2.0 mm.

12. The apparatus of claim 11, wherein the substrate comprises sapphire.

13. The apparatus of claim 11, wherein the substrate comprises glass.

14. The apparatus of claim 1, further comprising a fastener holding the substrate and the plate together in contact.

15. A method for determining whether a test compound solution induces progressive cell activity response, the method comprising:
    depositing a media containing cells into a cavity defined between a plate and a substrate,
    wherein the substrate has an inner surface and an outer surface opposite to the inner surface,
    wherein the plate has a first surface and a second surface opposite to the first surface, the second surface facing the inner surface of the substrate,
    wherein the plate defines a through-well extending from the first surface of the plate to the second surface of the plate,
    wherein the through-well exposes the inner surface of the substrate,
    wherein the through-well is in fluid communication with the cavity,
    wherein a hydrophobic barrier on the substrate and/or the plate defines a test site enclosing the through-well when the substrate and the plate are viewed from a plan view perpendicular to a plane defined by the plate,
    wherein, when viewed from the plan view, the test site is elongated, having a length greater than a width,
    wherein the hydrophobic barrier allows passage of gas outside of the test site while limiting passage of liquid outside of the test site,
    wherein the substrate, the plate, and the hydrophobic barrier are configured to contain the cells within the test site, wherein the through-well is disposed at a first side portion of the test site when viewed from the plan view, the test site having a second side portion opposite to the first side portion, wherein the plate and the substrate define a gap between the substrate and an edge of the through-well at the second surface of the plate, on a side of the through-well facing the second side portion of the test site, and wherein the gap extends substantially across the width of the test site;

allowing the media containing cells to wick into the cavity out to the hydrophobic barrier and form a meniscus at the gap;

placing the test compound solution in the through-well and in contact with the media containing cells at the meniscus at the gap;

diffusing into the media containing cells the test compound solution in a substantially linear front originating from the gap, spanning the width of the test site, and moving across the length of the test site from the first side portion of the test site to the second side portion of the test site, wherein a first cell of the media is closer to the gap than a second cell of the media;

allowing the test compound solution to diffuse into the media for a predetermined duration such that the first cell is exposed to the test compound solution longer than the second cell is exposed to the test compound solution;

after the predetermined duration, detecting a degree of activity of the first cell and a degree of activity of the second cell; and comparing the degree of activity of the first cell to the degree of activity of the second cell to determine the presence or absence of a progressive cell activity response by the cells of the media to determine whether the test compound solution induces progressive cell activity response.

16. The method of claim 15, further comprising depositing a gel in the cavity.

17. The method of claim 15, wherein the media containing cells comprises a gel.

18. The method of claim 15, wherein the length of the test site is at least two times greater than the width of the test site, to provide the substantially linear front.

19. The method of claim 15, wherein depositing the media containing cells into the cavity defined between the plate and the substrate comprises depositing the media containing cells in the through-well.

20. The method of claim 15, wherein the plate defines a second through-well in fluid communication with the cavity, and wherein depositing the media containing cells into the cavity comprises depositing the media containing cells in the second through-well.

21. The method of claim 15, wherein the hydrophobic barrier comprises a groove in the second surface of the plate and/or the inner surface of the substrate.

* * * * *